(12) United States Patent
Vuylsteke et al.

(10) Patent No.: US 6,300,071 B1
(45) Date of Patent: Oct. 9, 2001

(54) METHOD FOR DETECTING NUCLEIC ACID METHYLATION USING AFLP™

(75) Inventors: Marnik Johan Roger Vuylsteke, Ede; Petrus Antonius Josephina Vos, Renswoude; Marcus Florent Oscar Zabeau, Gent, all of (NL)

(73) Assignee: Keygene N.V., Wageningen (NL)

( * ) Notice: Subject to any disclaimer, the term of this patent is extended or adjusted under 35 U.S.C. 154(b) by 0 days.

(21) Appl. No.: 09/362,311

(22) Filed: Jul. 28, 1999

(30) Foreign Application Priority Data

Jul. 29, 1998 (EP) ................................. 98202549.6

(51) Int. Cl.$^7$ .............................. C12Q 1/68; C12P 19/34; C07H 21/04
(52) U.S. Cl. ........................... 435/6; 435/91.2; 536/24.2; 536/24.33
(58) Field of Search .................. 435/91.2, 6; 536/24.33, 536/24.2

(56) References Cited

FOREIGN PATENT DOCUMENTS

| 0534858 | 3/1993 | (EP) . |
| 9627024 | 9/1996 | (WO) . |
| 9745560 | 12/1997 | (WO) . |
| 9808981 | 3/1998 | (WO) . |

OTHER PUBLICATIONS

Reyna–Lopez, et al. "Differences in DNA methylation patterns are detectable during dimorphic transition . . . " Mol. Gen. Genet., 1997, 253: 703–710.*
Donini, et al. "AFLP fingerprinting reveal pattern differences between template DNA extracted from different plant organs" Genome 1997, 40:521–526.*
Stratagene catalog, 1988, p. 39.*
Chen et al., "Methylation of CpG island is not ubiquitous mechanism for the loss of oestrogen receptor in breast cancer cells", Medline abstract of Brit. J. Cancer, vol. 77, pp. 181–185, (1990).
Xiong et al., "Patterns of cytosine methylation in an elite rice hybrid and its parental lines, detected by a methylation–sensitive amplification polymorphism technique", Mol. Gen. Genet., vol. 261, pp. 439–446, (1999).
Vos et al., "AFLP: a new technique for DNA fingerprinting", Nucleic Acids Research, vol. 23, No. 21, pp. 4407–4414, (1995).

* cited by examiner

Primary Examiner—W. Gary Jones
Assistant Examiner—B J Forman
(74) Attorney, Agent, or Firm—Browdy and Neimark

(57) ABSTRACT

The invention relates to a method for analyzing of determining the methylation pattern of a starting DNA and/or for distinguishing between methylated and non-methylated sites in the starting DNA, comprising at least (A) generating a first DNA fingerprint, containing bands corresponding to both the methylated and non-methylated sites of interest; and/or (B) generating a second DNA fingerprint, containing bands corresponding only to the methylated sites of interest; and optionally comprising (C) generating a third DNA fingerprint, containing bands corresponding only to the non-methylated sites of interest; and optionally further comprising (D) analysing the fingerprint(s) thus obtained. The fingerprints are preferably generated using AFLP, by means of a frequent cutter and a methylation sensitive rare cutter. The invention further relates to specific methods for generating the above first and second DNA fingerprint by means of AFLP, and kits for use with said methods.

24 Claims, 8 Drawing Sheets

Fig 5
A:
B:
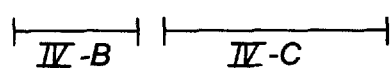
C:

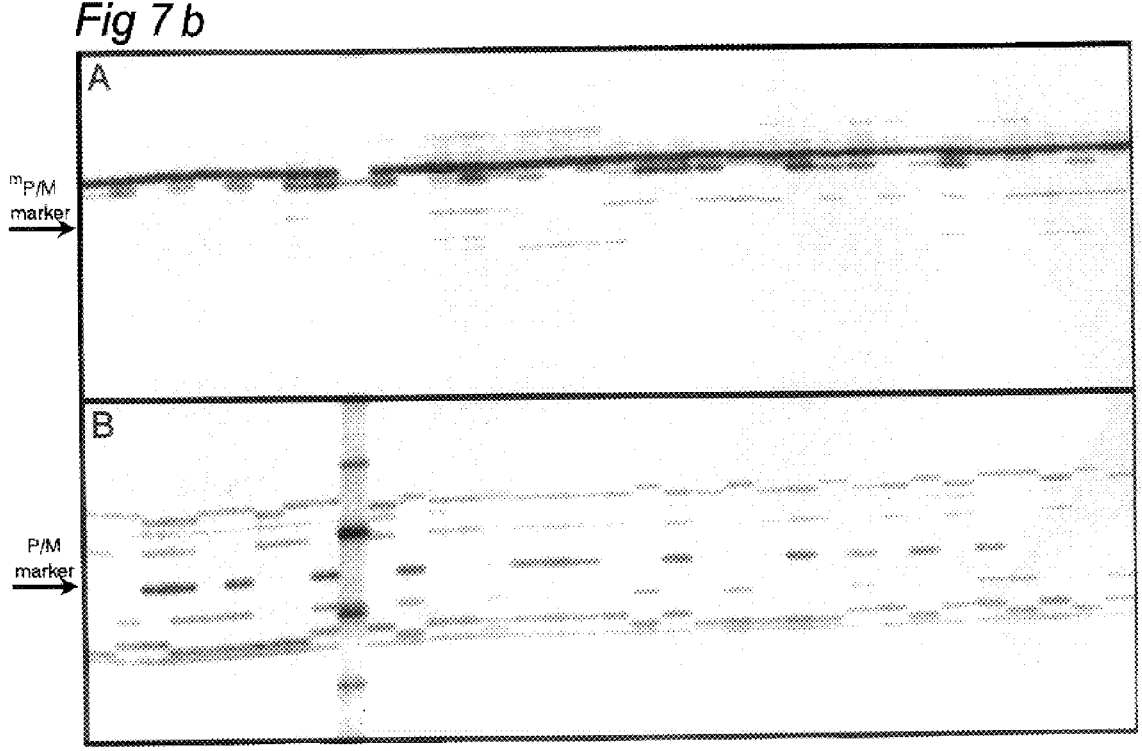

METHOD FOR DETECTING NUCLEIC ACID METHYLATION USING AFLP™

The present invention relates to a method for detecting DNA methylation using AFLP™. In particular, this method can be used to distinguish between methylated and non-methylated sites (nucleotides) in a nucleic acid, more particular between methylated and non-methylated restriction sites. Thus, the method of the invention can provide information on the methylation pattern of the DNA, which can be visualised as a DNA-fingerprint.

Selective restriction fragment amplification or AFLP is known, for instance from the European patent application 0 534 858 by applicant, incorporated herein by reference. In general, AFLP comprises the steps of:

(a) digesting a nucleic acid, in particular a DNA, with one or more specific restriction endonucleases, to fragment said DNA into a corresponding series of restriction fragments;

(b) ligating the restriction fragments thus obtained with at least one double-stranded synthetic ligonucleotide adapter, one end of which is compatible with one or both of the ends of the restriction fragments, to thereby produce tagged restriction fragments of the starting DNA;

(c) contacting said tagged restriction fragments under hybridizing conditions with at least one oligonucleotide primer;

(d) amplifying said tagged restriction fragments hybridized with said primers by PCR or similar technique so as to cause further elongation of the hybridized primers along the restriction fragments of the starting DNA to which said primers hybridized; and (e) identifying or recovering the amplified or elongated DNA fragment thus obtained.

The amplified DNA-fragments thus obtained can then be analysed and/or visualised, for instance by means of gel-electrophoresis. This provides a genetic fingerprint showing specific bands corresponding to the restriction fragments which have been linked to the adapter, have been recognized by the primer, and thus have been amplified during the amplification step. The fingerprint thus obtained provides information on the specific restriction site pattern of the starting DNA, and thus on the genetic make-up of the organism from which said DNA has been derived.

AFLP can therefore be used to identify said DNA; to analyse it for the the presence of specific restriction site patterns, restriction fragment length polymorfisms (RFLP's) and/or specific genetic markers (so-called "AFLP-markers"), which may be indicative of the presence of certain genes or genetic traits; or for similar purposes, for instance by comparing the results obtained to DNA-samples of known origin or restriction pattern, or data thereon.

The primers used in AFLP are such that they recognize the adapter and can serve as a starting point for the polymerase chain reaction. To this end, the primers must have a nucleotide sequence that can hybridize with (at least part of) the nucleotide sequence of the adapter adjacent to the 3' end of the restriction fragment to be amplified. The primers can also contain one or more further bases (called "selective bases") at the 3'-end of their sequence, for hybridization with any complementary base of bases at the 3'-end of the adapter ligated restriction fragment. As, of all the adapter ligated restriction fragments present in the mixture, only those fragments that contain bases complementary to the selective bases will subsequently be amplified, the use of these "selective" primers will reduce the total amount of bands in the final fingerprint, thus making the fingerprint more clear and more specific. Also, the use of different selective primers will generally provide differing fingerprints, which can also be used as a tool for the purposes of identification or analysis.

As AFLP provides amplification of both strands of a double stranded starting DNA, AFLP advantageously allows for exponential amplification of the fragment, i.e. according to the series 2, 4, 8, 16, etc.. Also, AFLP requires no prior knowledge of the DNA sequence to be analysed, nor prior identification of suitable probes and/or the construction of a gene library from the starting DNA.

For a further description of AFLP, its advantages, its embodiments, as well as the techniques, enzymes, adapters, primers and further compounds and tools used therein, reference is made to EP-0 534 858, incorporated herein by reference. Also, in the description hereinbelow, the definitions given in paragraph 5.1 of EP-0 534 858 will be used, unless indicated otherwise.

It is well known that the DNA of a prokaryotic or eukaryotic organism can contain methylated sites, i.e. that certain nucleotides of said DNA strands can be substituted with a methyl-group. In particular, cytosine residues, as well as adenine residues (in bacteria), can be methylated; for instance, in mammals, it is known that 2–7% of all cytosine-residues are methylated, and this may be as high as 30% in plants. Methylated cytosines can occur as mCG doublets, as small palindromic 5'-$^m$CpG -3'
3'-GpC$^m$-5' sequences, with both cytosine residues being methylated, or as $^m$CNG triplets (the latter particular in plants). Often, the majority of CG-sites in the DNA of both eukaryotes and bacteria are methylated.

In prokaryotic organisms, the pattern of DNA-methylation can be used to identify a particular bacterial strain or to distinguish replicated and non-replicated DNA (vide B. Lewin, GENES V, Oxford Univ. Press 1944, chapter 20). DNA-methylation also plays a role in DNA repair and the timing of DNA replication.

In eukaryotes, DNA-methylation is known to be involved in several genetic mechanisms, such as the regulation of gene expression, for instance through gene silencing or gene activation (vide B. Lewin, GENES V, Oxford Univ. Press 1994, chapter 28).

Also, in eukaryotes, DNA methylation is thought to be associated with genetic diseases through the mechanism of "imprinting", as well as increased susceptibility for mutagenesis and the origin of cancer. For instance, in female individuals, DNA-methylation, which is involved in X-chromosome activation/inactivation, can be used for distinguishing between neoplastic (clonal) cell populations and pseudoplastic or hyperplastic populations, to determine whether a growth of these cells is malignant or not (WO 96/27024). Also, the state of methylation of reporter genes has been used in in vivo mutagenicity assays (WO 93/17123 and the references cited therein).

Furthermore, changes in DNA-methylation can occur during gene transformation, making it possible to distinguish transformed and not-transformed genes or sequences. For instance, analysis of (the changes in) DNA methylation pattern has been used for the early detection of transgenic embryo's (WO 92/22647).

In plants, such as pea and tomato, methylation patterns can be used to distinguish between varieties by detecting restriction fragment length polymorphisms characteristic of these distinctive varieties (WO 90/05195). In tomato, this is carried out by digesting genomic DNA with a non-methylation sensitive restriction enzyme, and screening the fragments thus obtained by means of Southern hybridization using detectably labelled probes, said probes having been obtained by digestion of tomato genomic DNA with a methylation sensitive restriction enzyme. The bands in the resulting DNA-fingerprint enable identification of species specific, variety specific or individual RFLP's.

However, this method is not suited or intended for specifically distinguishing between methylated and non-methylated sites within the target DNA. Also, the genomic DNA to be analysed is itself not treated with a methylation sensitive restriction enzyme (these are only used in generating the probes). Furthermore, the technique described in WO 90/05195 does not involve any DNA-amplification step, and suffers from the general disadvantages of similar conventional RFLP detection techniques, such as low resolution, as well as being time consuming and laborious (compare EP-A-0 534 858, paragraph 2.1).

Nucleotide methylation using sequence specific methylases or restriction methylases has also been used as a tool for marking specific DNA strands or fragments. For instance, in WO 93/22462, thus marked DNA fragments are used in genomic mapping. Of course, when such methylation markers are used, a suitable technique for distinguishing methylated from non-methylated DNA fragments, or even specific methylated and non-methylated sites, is required for subsequent identification and tracking of the marked sequences.

For a further discussion of DNA methyation in prokaryotes and eukaryotes reference is made to the standard handbooks, to U.S. Pat. No. 4,405,760, WO 90/05195 and the further above cited appications, as well as the references cited therein, which are incorporated herein by reference.

It is known that certain restriction enzymes cleave their target sites according to the state of methylation thereof, for instance only when the target site is non-methylated. Such enzymes, well known examples of which are PstI, HpaII, MspI and ClaI, can be used to assess the state and/or degree of methylation of DNA-sequences, or the presence of specific methylated sites therein, by means of selective restriction of (generally) the non-methylated sites, followed by identification of the fragments obtained, usually by means of probing techniques (vide U.S. Pat. No. 5,405,760, DE-PS-293 139 and WO 93/22462). However, these methods are cumbersome, inaccurate, and generally require the development of suitable probes and/or at least some prior knowledge of the sequence to be analysed.

Other restriction enzymes, such as MseI, cut their target site irrespective of whether it is methylated or not. Although both types of restriction enzymes can be and are used in the AFLP technique described in EP-0 534 858 (vide for instance Example 2), this method is as such not suitable determining the methylation pattern of the starting DNA.

In view of the above, a quick and reliable method for obtaining information on the methylation pattern of starting or target DNA would be of great value to the art. Therefore, a method for distinguishing between methylated and non-methylated sites in a starting nucleic acid, and in particular for distinguising between methylated and non-methylated restriction sites of genomic DNA, has now been developed. In general, this method comprises at least:

(A) generating a first DNA fingerprint, containing bands corresponding only to the methylated sites of interest; or (B) generating a second DNA fingerprint, containing bands corresponding to both the methylated and non-methylated sites of interest; and further optionally comprises (C) generating a third DNA fingerprint, containing bands corresponding only to the non-methylated sites of interest; as well as (D) analysing and/or comparing the fingerprint(s) thus obtained; the respective fingerprints preferably being generated using an amplification technique, such as the AFLP technique described in EP-A-0 534 858.

By comparing at least two of the fingerprints resulting from (A), (B) and/or (C), information on the methylation pattern of a starting DNA can be derived, as will further be described hereinbelow.

Preferably, at least the fingerprints resulting from (A) and (B) are generated and compared to each other; more preferably, all three fingerprints resulting from (A), (B) and (C) are generated and compared to each other.

Conveniently, the above fingerprints can be generated in conjunction with each other, i.e. in parallel and more or less simultaneously, using the same pool or preparation of starting DNA, such as a preparation of intact genomic DNA directly as obtained from the organism of interest. The resulting DNA-fingerprints can then be run in separate lanes of the same electrophoresis gel, allowing immediate and easy comparison of the resulting patterns of bands. In this way, from one gel, information on the methylation pattern can directly be obtained. Also, each fingerprint can conveniently be generated in a "one pot reaction" using well-established AFLP-technology and equipment.

However, although for reasons of reliability and easy comparison, it is generally preferred to generate and run the above fingerprints together, preferably starting from the same DNA or DNA-preparation, such as a preparation of intact genomic DNA as isolated from the organism of interest, it is also possible to compare the patterns generated from (1) and/or (2) to known DNA-fingerprints or earlier obtained results, such as a database. This equivalent method is also encompassed within the scope of the present invention. Also, it should be understood that instead of the preferred method of generating a DNA-fingerprint, equivalent methods for anaysing and/or visualising restriction fragment mixtures, in particular on the basis of differences in size/molecular weight of the various fragments generated, can also be used, as will be clear to the skilled person.

Further aspects of the invention reside in the way in which the above indicated DNA fingerprints are obtained, as well as AFLP-methodology used therein. Other aspects reside in the amplified fragments or mixtures of fragments that are obtained according to the methods (A) and (B) described below.

Yet another aspect comprises any data generated by the method of the invention, optionally on a suitable data carrier, such as paper or a computer disk. This includes the generated DNA-fingerprints (including the gels), photographs or other reproductions thereof, as well as (stored) analog or digital data thereon.

The invention also comprises kits for use in the invention, comprising at least: a frequent cutter restriction enzyme; a methylation sensitive rare cutter restriction enzyme; (at least) a first and second adapter for use with the frequent cutter; and (at least) a first and second adapter for use with the rare cutter; as well as primers for use with these adapters; wherein these components are essentially as described herein.

The kits can further contain all known components for AFLP kits, such as restriction enzymes (in which case the adapters are preferably suited to be ligated to the restrictes sites generated with said enzyme); a polymerase for amplification, such as Taq-polymerase; nucleotides for use in primer extension; as well as buffers and other solutions and reagentia; manuals, etc.. Further reference is made to the European patent application 0 534 858, incorporated herein by reference.

Also, it should be noted that the method of the invention comprises and/or combines several features, which as such could also be used in other AFLP-techniques and/or applications, as will be discussed hereinbelow. These form separate aspects of the invention.

The method of the invention will be illustrated by means of the enclosed figures, in which FIG. 1 schematically shows the general method (A) for obtaining a DNA fingerprint showing only the methylated sites; and FIG. 2 schematically shows the general method (B) for obtaining a DNA fingerprint showing both the methylated and non-methylated sites;

FIG. 3 schematically shows a general method for obtaining a DNA fingerprint containing only the non-methylated sites.

FIG. 5 shows the differences in the essential bands obtained in the methods of FIGS. 1, 2 and 3.

Figure 1:
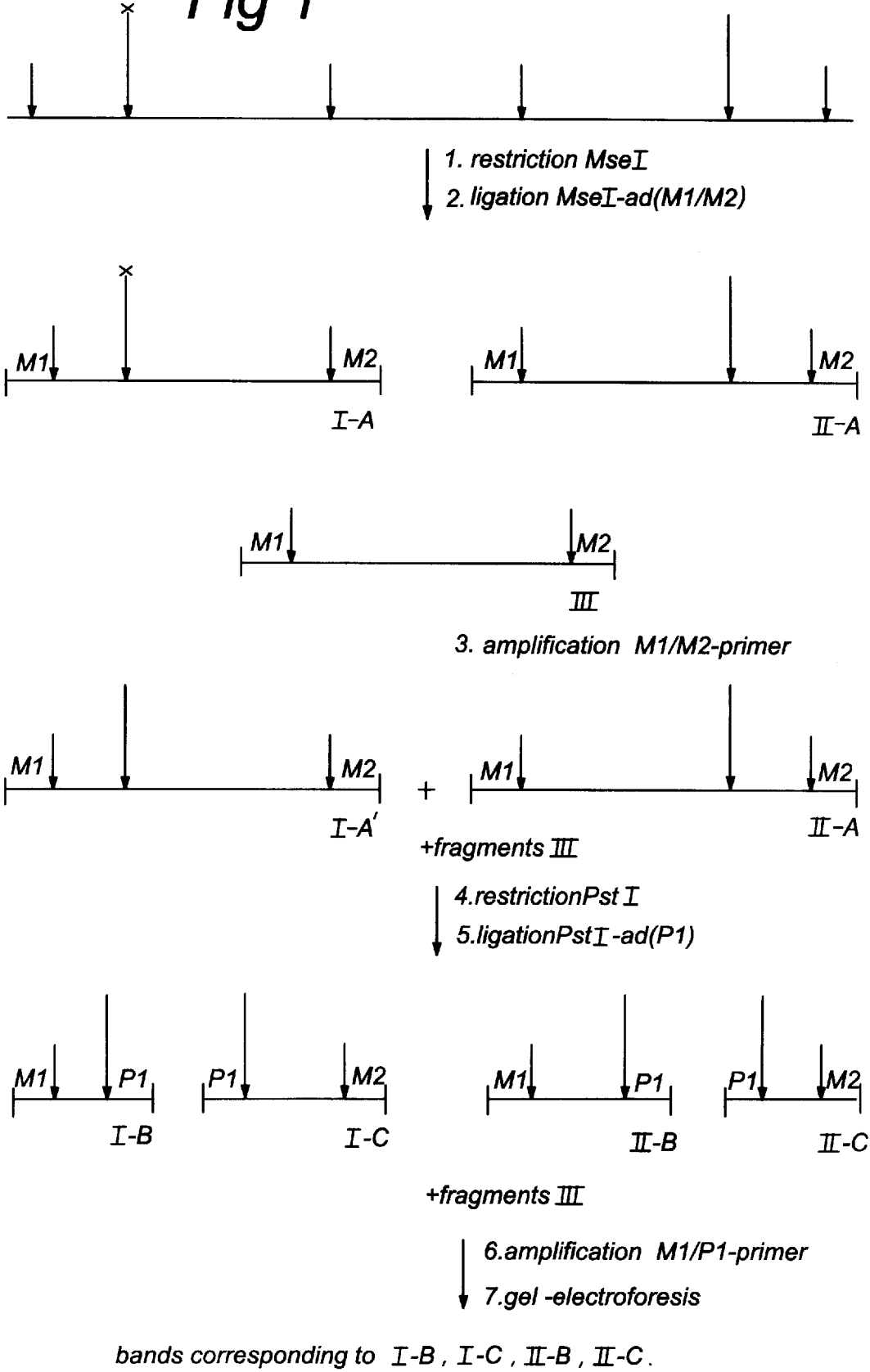
Figure 2:
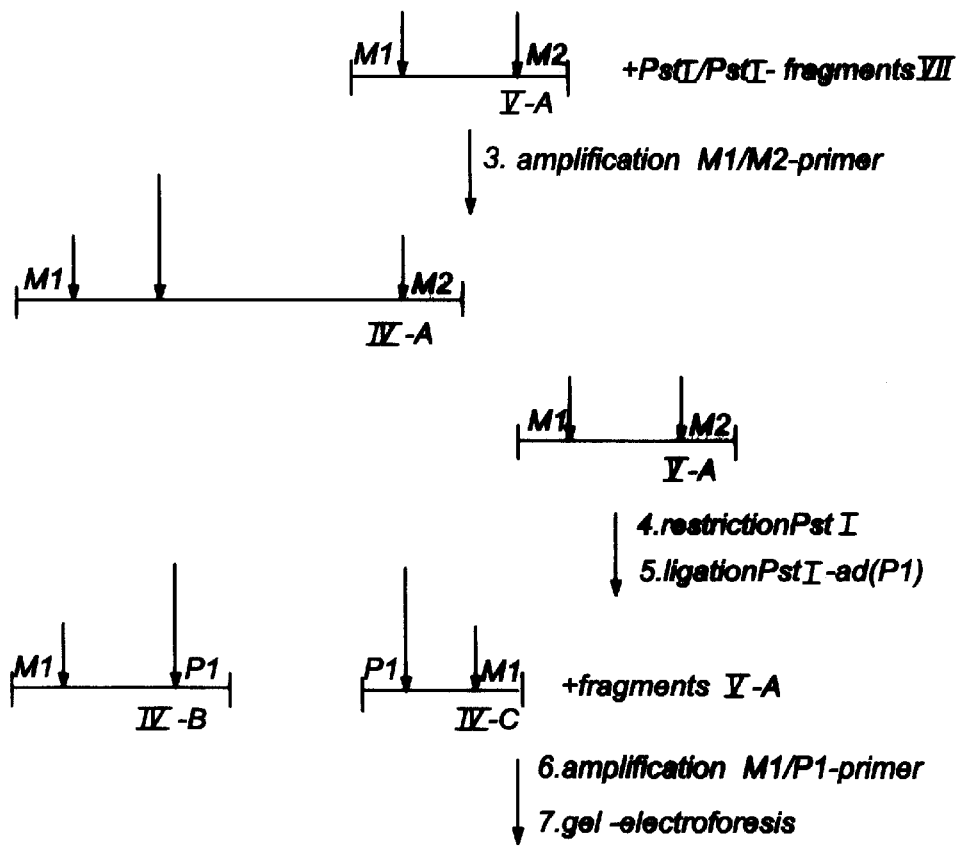
Figure 3:
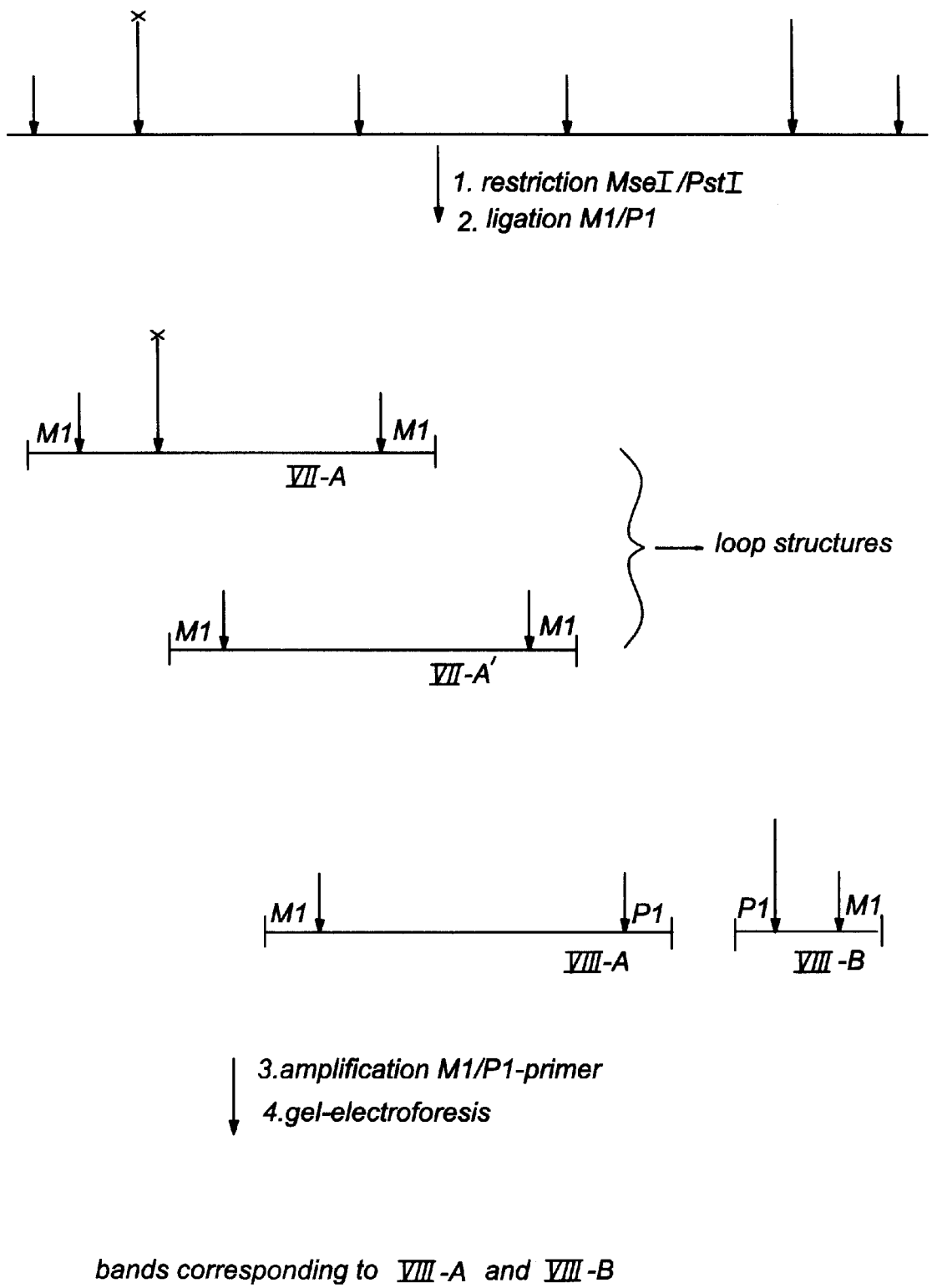
Figure 6:
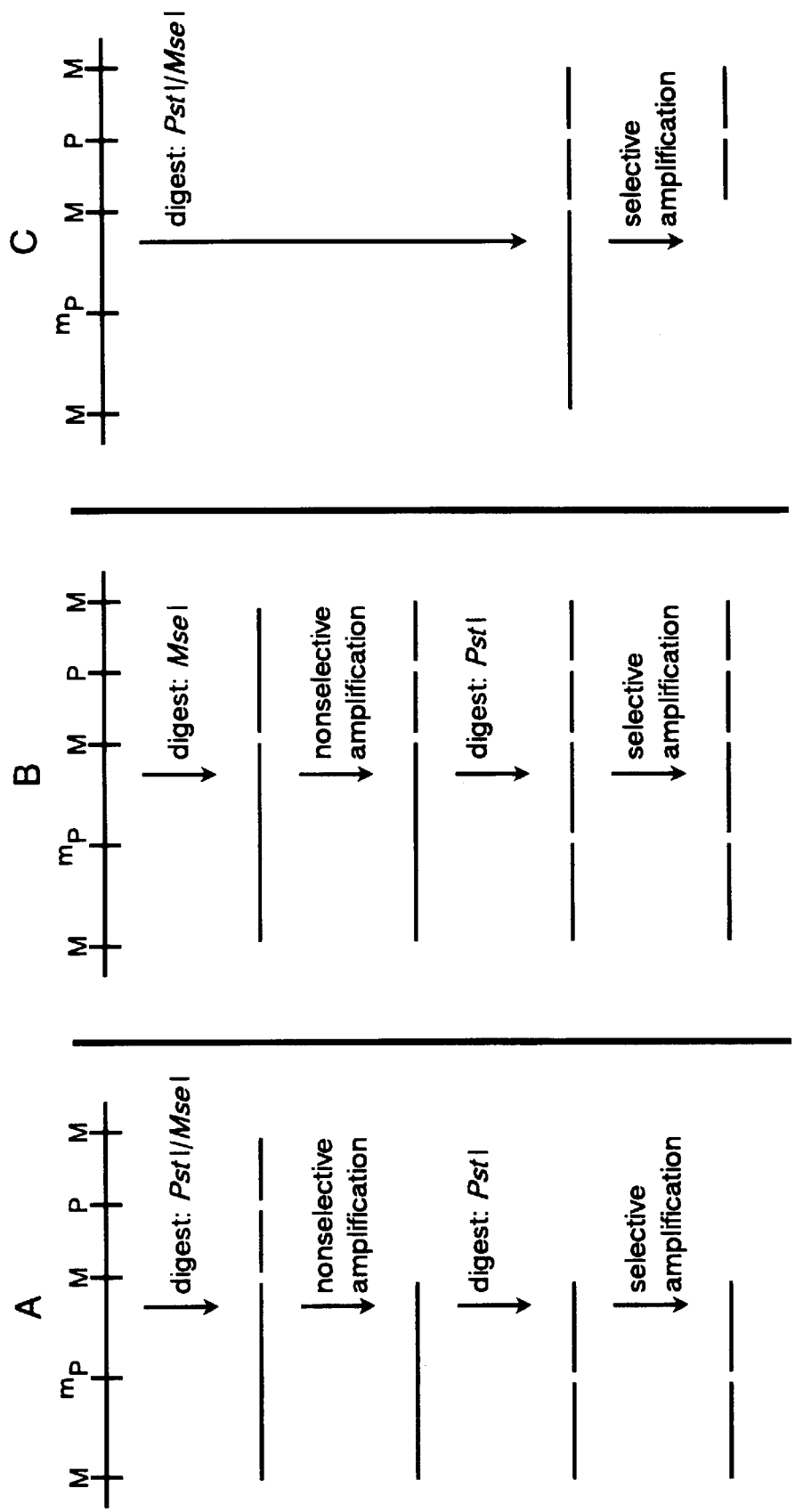

FIG. 6 gives a general schematic representation of the method of the invention for the enzyme combination (EC) PstI/MseI, in which the above methods A, B and C (as shown in FIGS. 1–3) are shown side-by-side.

Figure 7A:
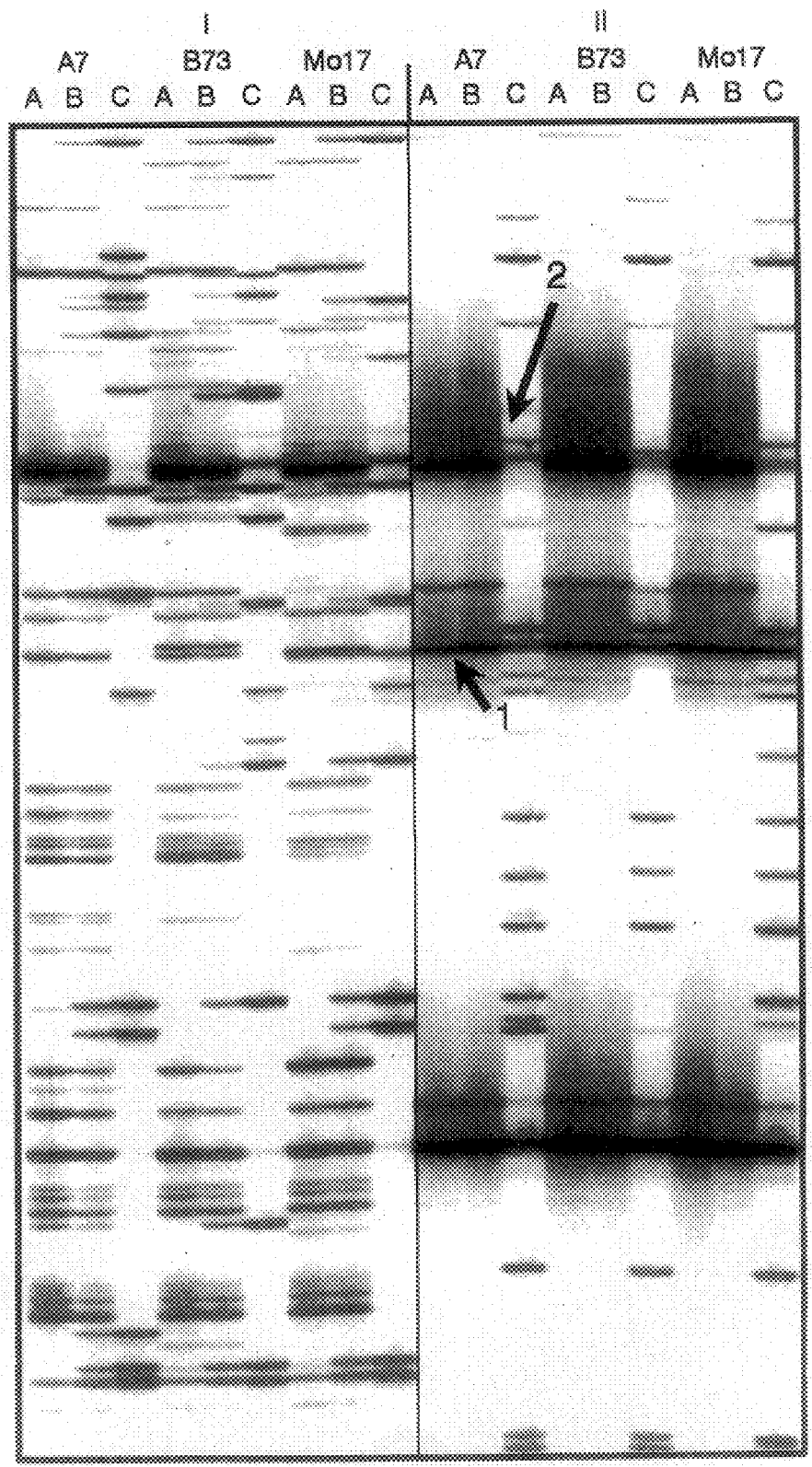

FIGS. 7A and B show methylation AFLP fingerprints FIG. 2 shows a number of typical methylation AFLP fingerprints obtained with the two step amplification strategy of genomic DNAs from the three maize inbred lines A7, B73 and Mo17.

FIGS. 8A and 8B are DNA fingerprints showing the segregation of (A) PstI/MseI '"AFLP markers and (B) PstI/MseI AFLP markers in a Recombinant Inbred (RI) population derived from a cross of two maize lines.

The starting DNA used in the invention can be any DNA, which contains, is suspected to contain, or is to be investigated for, DNA-methylation (including hemi-methylated DNA). Usually, native methylated DNA, in particular genomic DNA, will be used; when genomic DNA is used, the method of the invention will generally be used to distinguish between native methylated and native non-methylated sites, in which case method (A) above will be used to generate a first DNA fingerprint, containing bands corresponding only to the native methylated sites of interest; method (B) above will be used to generate a second DNA fingerprint, containing bands corresponding to both the native methylated and native non-methylated sites of interest; and method (C)—if applied—will be used to generate a third DNA fingerprint, containing bands corresponding only to the native non-methylated sites of interest.

The starting DNA can be derived from any suitable source, such as prokaryotic or eukaryotic organisms (including viruses, yeasts and bacteria), depending upon the intended application. Preferably, eukaryotic DNA, more preferably plant or animal (including human) derived DNA, is used. Also, DNA that has been provided with methylation (i.e. as a marker) or that has been subject to a methylating treatment, can be used.

Furthermore, instead of a DNA, the invention can be applied to other types of methylated nucleic acids, such as methylated single strand RNA that can occur naturally in the cell.

In the method of the invention, two different restriction enzymes are used: one enzyme which serves the purpose of reducing the size of the restriction fragments to a range of sizes which are amplified efficiently, hereinbelow referred to as the "frequent cutter", and another enzyme which serves the purpose of targeting rare sequences, hereinbelow referred to as the "rare cutter". For the terms cutter and frequent cutter, reference is also made to EP-A-721 987 by applicant, incorporated herein by reference.

At least one of the enzymes used must be sensitive to (the state of) methylation of the intended site, i.e. be able to distinguish between methylated and non-methylated sites on the target DNA. In practice, generally a methylation-sensitive rare cutter is used.

Examples of suitable frequent cutter enzymes are MseI and TaqI.

Examples of commercially available suitable methylation-sensitive rare cutters are PstI, HpaII, MspI, ClaI, HhaI, EcoRII, BstBI, HinPI, MaeII, BbvI, PvuII, XmaI, SmaI, NciI, AvaI, HawII, SalI, XhoI and PvuII, of which PstI, HpaII, MspII, ClaI, EcoRII, BstBI, HinPI and MaeII are preferred. Other suitable restriction enzymes are for instance described in U. S. Pat. No. 5,487,994, U.S. Pat. No. 5,340,733, or will be clear to the skilled person. Methylation-sensitive mutants of these and other restriction enzymes can also be used.

For analysis of eukaryotic genomic DNA, preferably C-methylation sensitive restriction enzymes are used. Also, in the practice of the invention, generally restriction enzymes will be used that restrict the non-methylated sites, but not the corresponding methylated sites. However, enzymes which restrict the methylated sites, and not the corresponding non-methylated sites, such as DpnI, can also be used analogously.

Of the above restriction enzymes, the use of those enzymes which, after digestion, leave the restricted double stranded DNA with a protruding 3'-end, such as PstI, are preferred, for reasons which will be discussed hereinbelow.

Generally, only one frequent cutter and one rare cutter will be used in generating the fingerprints resulting from (A), (B) and/or (C). However, the use of more than one frequent cutter, and in particular of more than one rare cutter, is also encompassed within the invention. Also, in order to enable comparison of the fingerprints obtained, the restriction enzymes used in generating the fingerprints resulting from (A), (B) and/or (C) should generally be the same, although the use of different enzymes in these methods is encompassed within the scope of the invention, so long as the fingerprints obtained allow comparison to each other or to known data, or otherwise provide information on the methylation of the starting DNA.

For reasons of convenience, the invention will be further illustrated hereinbelow using the non-limiting combination of the frequent cutter MseI and the methylation sensitive rare cutter PstI. It should however be understood that any other suitable combinations of frequent cutters and rare cutters, for instance chosen from the enzymes mentioned above, can also be used.

Also, it should be understood that although the procedures (A), (B) and (C) constitute the most convenient and preferred modes of generating the data (fingerprints) on the methylation pattern, equivalent methods or steps, in particular equivalent amplification techniques, can also be used, so long as the obtained results provide information on the methylation of the starting DNA.

The method of the invention can further be carried out using well known techniques of genetic manipulation, such as described in Sambrook et al, "Molecular Cloning: A Laboratory Manual" (2nd. ed.). Vols. 1–3, Cold Spring Harbor Laboratory (1989) as well as F. Ausubel et al, eds., "Current protocols in molecular biology", Green Publishing and Wiley Interscience, New York (1987), as well as standard AFLP methodology and equipment, which are used in a manner known per se or analogously thereto. For AFLP, reference is again made to EP-A-0 534 858, incorporated herein by reference. The restriction enzymes and other commercially available products are generally used according to the manufacturers guidelines.

A. Method for producing a fingerprint containing bands corresponding to the methylated sites.

This aspect of the invention comprises:

1. restricting the starting DNA with a frequent cutter and a methylation sensitive rare cutter;
2. ligating the restriction fragments thus obtained to a first and second adapter for the frequent cutter, as well as a first adapter for the rare cutter;
3. amplifying the mixture thus obtained, using primers for the first and second frequent cutter adapter;
4. restricting the amplified fragments thus obtained using a methylation sensitive rare cutter;
5. ligating the restriction fragments thus obtained to a second adapter for the methylation sensitive rare cutter;
6. amplifying the restriction fragments thus obtained using a primer for the first or second frequent cutter adapter, and a primer for the second rare cutter adapter;
7. optionally analysing the mixture of amplified fragments thus obtained in a manner known per se, preferably by generating a DNA fingerprint.

Method (A) is schematically outlined in FIG. 1 and (together with methods B and C) in FIG. 5, which both show a starting DNA (generally full length—i.e. uncut-genomic DNA) containing frequent cutter (MseI) sites, as well as methylated and non-methylated rare cutter (PstI) sites.

In step 1, the starting DNA is restricted using both the frequent cutter MseI and the rare cutter PstI, in a manner known per se. This restricts both the MseI sites and the non-methylated PstI-sites, but leaves the methylated PstI-sites intact. Preferably, the PstI- and MseI-restrictions are carried out simultaneously using a mixture of these enzymes, although it is also possible to use two separate restriction steps.

In step 2, the restricted mixture is ligated to adapters, also in a manner known per se, using a mixture of two different MseI-adapters, i.e. a "first" and a "second" MseI adapter, as well as a first PstI-adapter (Said adapters are indicated as "M1", "M2" and "P1" in FIGS. 1–4, respectively. The terms "first", "second" adapter/primer etc. are only used in this disclosure to denote/distinguish the different adapters/primers used. As such, any adapter/primer which meets the requirements set out below can be used as either the first, the second or any further primer/adapter.)

Figure 4:
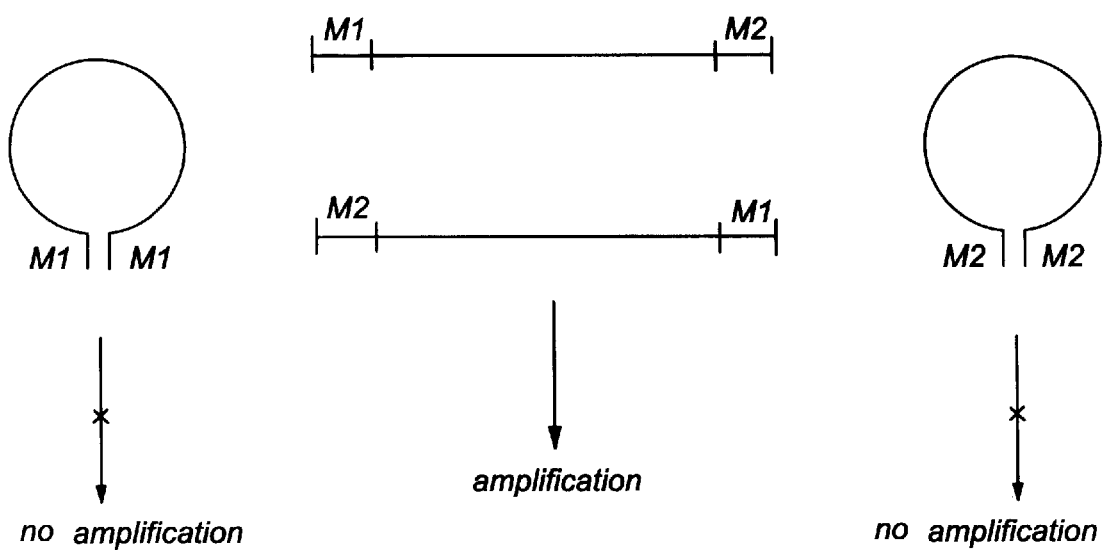
FIG. 4 shows the formation of single strand DNA loop structures in fragments of suitable length that have been ligated to the hybridizing or the same adapter at each end.

The first and second MseI-adapter, as well as the first PstI adapter are essentially as described in EP-A-0 534 858, or analogous thereto, in that they are suited for use as an adapter in AFLP and that they can be ligated to the cut ends of the MseI-fragments or PstI fragments respectively. In the method of the invention, the first and second MseI-adapter used are further preferably such that they cannot hybridize with one another under the conditions used. This prevents the formation of DNA-loop structures, as shown in FIG. 4, which can hinder amplification of the fragment. Preferably, the first and second MseI-adapters are used about equal amounts. The amount of PstI adapter (as compared to the amount of MseI) can generally be suitably chosen by the skilled person.

After ligation of the abovementioned adapters, a mixture of different restriction fragments is obtained. For the purposes of the invention, these can be distinguished in the following types.

MseI/MseI-fragments, which either do (indicated as I-A in FIG. 1) or do not (indicated as II-A in FIG. 1) contain a non-restricted methylated PstI-site. Of these fragments, in FIG. 1, only those with the different MseI-adapters at each end are shown. Fragments with the same MseI-adapter at each end (not shown) will also be obtained, but these will not be amplified efficiently due to the loop formation described above.

pstI/MseI-fragments, which contain either the first or second MseI-adapter at one end, and the first PstI-adapter at the other (of these two, in FIG. 1, only the fragment with the first MseI-adapter are shown as III-A/III-B). Rarely, these fragments can also contain a non-restricted methylated PstI-site. -PstI/PstI-fragments (shown as IV-A in FIG. 1). These fragments, which may or may not contain a further methylated PstI-site, will be extremely rare, and in general much longer than the MseI/MseI-fragments, I-A/II-A or the PstI/MseI-fragments III-A, due to the relative abundance of MseI-sites in the genome.

As will be clear to the skilled person, there will generally be several different fragments of each type present in the mixture obtained after adapter ligation, with differing lengths or differing positions of the non-restricted methylated PstI-sites, depending upon the restriction site and methylation pattern of the starting DNA. [Also, it should be understood that for each MseI/MseI fragment shown in FIG. 1, there is a corresponding fragment (not shown) in which the first and second MseI adapter are reversed (i.e. bound to the opposite ends of the fragment). For the purposes of the present method, these can essentially be considered equivalent to the fragments shown in FIG. 1, as will become clear hereinbelow.]

In step 3, the mixture of fragments obtained in step 2 is amplified, using a mixture of primers for the first and second MseI-adapter. These primers again are essentially as described in EP-A- 0 534 858, or analogous thereto, in that they are suited for use as a primer in AFLP and that they can be hybridize with the first and second MseI-adapters used, respectively. The number of selective nucleotides required in a specific primer/for a specific application may be species-dependant.

The amplification itself can be carried out in a manner known per se, such as described in EP-A-0 534 858 or in a manner analogous thereto, and is preferably carried out as a (pre)amplification using nonselective primers, i.e. containing no selective necleotides at the 3'-end of the primer sequence, or at most one selective base. Preferably, the first and second primer are used in about equal amounts.

During this amplification step, only the MseI-MseI fragments I-A, and II-A, which do or do not contain a methylated PstI-site—depending upon the original DNA and the position of the MseI and methylated PstI sites thereon—will be amplified exponentially and effectively. As no PstI-primers are used, the PstI/MseI-fragments III-A will only be amplified linearly, and the PstI/PstI-fragments IV will not be amplified at all.

Also, as the amplification is carried out in a medium containing only non-methylated nucleotides, the fragments I-A lose their methylation imprint; the corresponding non-methylated fragments as obtained after amplification are indicated as I-A' in FIG. 1. These I-A'-fragments can now be restricted using PstI in the subsequent restriction step 4. This restriction will not affect the fragments II-A, which originally did not contain any PstI site.

Also, in said step 4, as the amplified fragments thus obtained are now non-methylated, instead of a methylation-sensitive restriction enzyme, a methylation insensitive isoschizomer thereof that cuts the same (non-methylated) restriction site can also be used. For instance, when the methylation sensitive EcoRII is used, in step 4 its methylation-insensitive isoschizomer BstNI can be used.

After said restriction step 4, the PstI-cut ends of the restricted fragment I-A' are ligated in step 5 to a second PstI-adapter, the original fragment I-A providing two fragments I-B and I-C, which contain the second PstI-adapter on one end, and either the first or second MseI-adapter on the other. [In fact, as there are originally two equivalent fragments I-A described above, which only differ in the end at which the first and second MseI-adapter, respectively, are bound, also two pairs of equivalent fragments I-B and I-C are obtained (not shown), which have corresponding lengths but only differ in the MseI-adapter opposite to the second PstI-adapter. As will become clear below, for the purposes of the present method, these fragments can be considered equivalent to fragments I-B and I-C, and will not be further distinguished].

The second PstI adapter (indicated as "P2" in FIGS. 1–4) is again essentially as described in EP-A-0 534 858, or analogous thereto, in that it is suited for use as an adapter in AFLP and that they can be ligated to the PstI cut ends of fragments I-B and I-C. However, the second rare cutter adapter should differ from the first adapter, i.e. not be able to hybridize with the first rare cutter adapter under the conditions used. Also, as mentioned below, the second PstI adapter is preferably the same as the third PstI primer used in step 5 of method B below.

The respective lengths of fragments I-B and I-C depend upon the length of the original fragment I-A and the position of the methylated PstI-site therein; usually fragments I-B and I-C will differ from each other in length/molecular weight, and will also differ in length/molecular weight from the non-restricted fragments II-A, so that these fragments can be distinguished using a suitable technique.

To this end, the mixture is amplified in step 6 using suitable primer for the second PstI-adapter, as well as at least one suitable primer for the first and/or second MseI-adapters.

Most preferably, besides the PstI-primer, only one MseI-primer (i.e. for either the first or the second MseI-adapter) as used. In this way, only the fragments containing a PstI-adapter at one end, and the corresponding MseI-adapter at the other end will be amplified exponentially. Other fragments present in the mixture will only be amplified linearly and/or less efficiently, or even not at all, either due to loop formation or because only one or none of the primers required for exponential amplification is available, which will reduce both the total number of bands in the final fingerprint, as well as the number of non-informative bands.

The amplification step itself can be carried out in a manner known per se, such as described in EPA-0 534 858 or in a manner analogous thereto, and is preferably carried out as a two-step amplification, the first of which is a (pre)amplification using a primer for the second PstI-adapter with one selective nucleotide at the 3'-end of the primer sequence and a primer for the first (resp. second) MseI-adapter with one selective nucleotide at the 3'-end of the primer sequence (so called+1 primers). This is followed by amplification using selective primers for the second PstI-and first (resp. second) MseI-adapter, for instance using primers containing three selective nucleotides at the 3'-end (+3 primers). In both the pre-amplification and the final amplification, the respective printers can be used in about equal amounts.

In step 6, the number of selective nucleotides required in a specific primer for a specific application may be species-dependant. For instance, in maize, +2/+3 amplification and the double +3/+3 selectivity for the PstI/MseI primer combination (PC) may be used.

The resulting amplified fragments are then visualized using a suitable technique, such as the formation of a DNA fingerprint through gel electrophoresis. This fingerprint will show at least bands corresponding to fragments of types I-B and I-C, which through comparison with fingerprints generated according to method (B) or (C) or with known date can provide information on the methylaton pattern of the starting DNA, as further discussed below.

The fingerprint can again contain other minor and/or less informative bands, which—although they can still provide some useful information on the starting DNA—are not critical for the purposes of the invention. These bands will generally not interfere with the information essential for the purposes of the invention.

B. Method for producing a fingerprint containing bands corresponding to both the methylated and the non-methylated sites.

This aspect of the invention comprises:
1. restricting the starting DNA with a frequent cutter;
2. ligating the restriction fragments thus obtained with a third and fourth adapter for the frequent cutter;
3. amplifying the mixture thus obtained, using primers for the third and fourth adapter for the frequent cutter;
4. restricting the amplified fragments thus obtained using a methylation-sensitive rare cutter;
5. ligating the restriction fragments thus obtained to a third adapter for the methylation sensitive rare cutter;
6. amplifying the mixture thus obtained, using a primer for the third methylation sensitive rare cutter adapter, as well as a primer for the third or fourth frequent cutter adapter;
7. optionally analysing themixture of amplified fragments thus obtained in a manner known per se, preferably by generating a DNA fingerprint.

Method (B) is schematically outlined in FIG. 2, which shows a DNA fragment containing frequent cutter (MseI) sites (again indicated as minor arrows in the sequence), as well as methylated (large arrow with cross) and non-methylated (large arrow) rare cutter (PstI) sites.

In method (B), the third and fourth frequent cutter adapter and the second third rare cutter adapter are again essentially as described in EP-A-0 534 858, or analogous thereto, in that they are suited for use as an adapter in AFLP and that they can be ligated to the cut ends of the frequent cutter and rare cutter fragments, respectively. The two frequent cutter adapters are preferably again such that they cannot hybridize with one another under the conditions used, in order to prevent undesired loop formation.

The third and fourth cutter adapters can differ in sequence and/or number of nucleotides from the first and second frequent cutter adapter used in method (A) above, or method (C) below. Preferably, however, for reasons of convenience and in order to minimize the total amount of different adapters required in carrying out the invention, the third and fourth adapter for the frequent cutter restriction enzyme are the same as the first and second frequent cutter adapter used above, respectively. This also allows an even more direct comparison of the fingerprints obtained, thus making the entire method even more reliable.

Also, although the third rare cutter adapter can differ in both sequence and number of nucleotides from the first and second rare cutter adapter used in method (A), preferably the third frequent cutter adapter used in method (B) is the same as the second rare cutter adapter used in step 5/6 of method (A) above.

Hereinbelow, in accordance with these preferred embodiment, the third and fourth frequent cutter adapter and the third rare cutter adapter will be denoted hereinbelow as the "first and second" MseI primers and the "second" PstI-primer.

In step 1, the starting DNA is restricted using the frequent cutter MseI, in a manner known per se. This restricts the MsI-sites but leaves both the methylated and non-methylated PstI-sites intact.

In step 2, the restricted mixture is ligated to adapters, also in a manner known per se, using a mixture of the and second MseI-adapters.

After ligation of the frequent cutter adapters, a mixture of different restriction fragments is obtained. Of these fragments, in FIG. 1, only the fragments containing different MseI adapters at each end are shown. It should however be understood that corresponding fragments (not shown) containing either the first or the second frequent cutter adapter at both ends of the fragment are also obtained. Due to the loop formation mentioned above, these fragments will not be amplified efficiently during the subsequent amplification step.

Of the fragments containing the first and the second frequent cutter adapter shown in FIG. 2, for the purposes of the present method, three different types of fragments can be distinguished, i.e. one type containing the methylated PstI-site(s) (indicated as V-A in FIG. 2), a second type containing the originally non-methylated PstI-site(s) (indicated as VI-A in FIG. 2), and a third type containing PstI-sites (indicated as VII in FIG. 2).

As above, there will again be several different fragments of each type present in the mixture obtained after adapter ligation, with differing lengths and/or (in fragments V-A and VI-A) position of the PstI-sites, depending upon the restriction site pattern and methylation pattern of the starting DNA. [Also, it should again be understood that for each fragment type shown in FIG. 2, there is a corresponding fragment (not shown) in which the first and second adapter are reversed (i.e. bound to the opposite ends as shown in FIG. 2). For the purposes of the present method, these can essentially be considered equivalent to the fragments shown in FIG. 2, as will become clear hereinbelow.]

In step 3, the mixture of fragments obtained in step 2 is amplified, using a mixture of primers for the first and second MseI-adapter. These primers again are essentially as described in EP-A-0 534 858, or analogous thereto, in that they are suited for use as a primer in AFLP and that they can hybridize with the first and second MseI-adapters used, respectively. Again, the number of selective nucleotides required in a specific primer/for a specific application may be species-dependant.

Also, it should be noted that for methods (A), (B) and (C), where possible the primers used in conjunction with each of the respective adapters are preferably essentially the same for each of the adapters used, in that they have the same sequence in the region for hybridization with the adapter, and may only differ in the presence of the selective bases at their 3'-end, i.e. the number thereof and/or the specific nucleotides. This enables the same primers to be used, or the primers to be synthesised in conjuction with each other and/or starting from the corresponding non-selective primer sequence, so that a limited number of starting materials (primers) are required for carrying out the three methods of the invention.

The amplification itself can be carried out in a manner known per se, such as described in EP-A-0 534 858 or in a manner analogous thereto, and is preferably carried out as a (pre)amplification using nonselective primers, i.e. containing no selective nucleotides at the 3'-end of the primer sequence, or at most one selective base. Preferably, the first and second primer are used in about equal amounts.

During the amplification step, exponential amplification of all fragments containing two different MseI-adapters is obtained. Due to the loop-formation described above, fragments containing the same MseI-adapter at each end are not, or less efficiently amplified, and thus are present in minor amounts in the amplified mixture, which do not interfere with the remainder of the procedure.

Also, as the amplification is carried out in a medium containing only non-methylated nucleotides, the methylated fragments V-A lose their methylation imprint during amplification; the corresponding non-methylated fragments as obtained after amplification are indicated as V-A' in FIG. 2. These V-A'-fragments can now be restricted sing PstI in the subsequent restriction step 4, together with the amplified fragments VI-A containing the originally non-methylated PstI-sites.

Again, in said step 4 of method (A) above, instead of a methylation-sensitive restriction enzyme, a methylation insensitive isoschizomer thereof that cuts the same (non-methylated) restriction site can also be used.

After said restriction step 4, the PstI-cut ends of the restricted fragments are ligated to the third PstI-adapter, again providing a mixture of different adapter-containing restriction fragments, as shown in FIG. 2. The third PstI-adapter is again essentially as described in EP-A-0 534 858, or analogous thereto, in that it is suited for use as an adapter in AFLP and that it can be ligated to the cut ends of the PstI-fragments. Also, as mentioned, the third PstI adapter is preferably the same as the second PstI primer used in step 5 of method A above, and is so indicated below.

After ligation, the fragment(s) V-A/V-A' will essentially provide two restriction fragments (V-B and V-C), each containing the second PsfI-adapter at one end, and either the first or second MseI-adapter on the other end. These fragments will differ in length dependent on the position of the methylated PstI-site in the original MseI fragment V-A. [Again, as with fragments I-A and I-B/I-C in method (A) above, it should be understood that for each the fragments V-B and V-C shown in FIG. 2 (i.e. containing either the first or second MseI adapter), there will be two corresponding fragments (not shown) which contain the opposite MseI-adapter (i.e. containing the second or first MseI adapter, respectively). Of these four fragments, generally only the two fragments containing the first (or the second) MseI-adapter will be amplified in step 6 below.]

Correspondingly, the fragment(s) VI-A, which originally contained the non-methylated PstI-site, also two different fragments (VI-B and VI-C) are obtained, with different lengths depending on the position of the non-methylated PstI-site in the original MseI-fragment VI-A. [As with fragment V-A and V-B/V-C, in practice two pairs of equivalent fragments with the same length, but with either the first or the second MseI-adapter opposite the PstI-adapter, are obtained, which again are essentially equivalent and will not be distinguished below].

The mixture obtained after restriction with PstI and ligation of the PstI-adapter will further contain the MseI fragments VII that originally did not contain either a methylated or non-methylated PstI-site.

In principle, all fragments V-B, V-C, VI-A, VI-B, as well as the fragments VII will have differing lengths/molecular weights, so that they can be distinguished using a suitable technique.

To this end, the mixture is amplified in step 6 using suitable primer for the second PstI-adapter, as well as at least one suitable primer for the first and/or second MseI-adapters. These primers are again essentially as described in EP-A-0 534 858, or analogous thereto, in that they are suited for use as a primer in AFLP and that they can be hybridize with the second PstI-adapter, and the first and/or second MseI-adapter, respectively. Preferably, selective primers are used.

As mentioned above, these primers are preferably the same as the corresponding primers used in step 6 of method A above. Also, for the reasons given in method A, most preferably only one MseI-primer (i.e. for either the first or the second MseI-adapter) is used, besides the primer for the first PstI-adapter. Also, it should be noted that, as no primers for the second PstI-adapter are used in step 6, the PstI/MseI-fragments VI generated in the first restriction step of method B will again only be amplified linearly.

The amplification step itself can be carried out in a manner known per se, such as described in EP-A-0 534 858 or in a manner analogous thereto, and is preferably carried out as the two-step amplification of step 6 of method A above, i.e. as a +1/+1 (pre)amplification (PstI+1/MseI+1), followed by a +2/+3 or +3/+3 amplification (PstI+2/MseI+3 or (PstI+3/MseI+3). In both the pre-amplification and the final amplification, the respective primers can be used in about equal amounts.

Again, as in step 6 of method (A), the number of selective nucleotides required in a specific primer for a specific application may be species-dependant. For instance, in maize, +2/+3 amplification and the double +2/+3 selectivity for the PstI/MseI primer combination (PC) may be used.

The resulting amplified fragments are then visualized using a suitable technique, such as the formation of a DNA fingerprint through gel electrophoresis. This fingerprint will show at least bands corresponding to fragments of types V-B, V-C, VI-B and VI-C, which through comparison with fingerprints generated according to method (A) or (C) or with known data can provide information on the methylaton pattern of the starting DNA, as discussed below.

The fingerprint can also contain other minor and/or less informative bands, which—although they can still provide some useful information on the starting DNA—are not critical for the purposes of the invention. These bands will generally not interfere with the information essential for the purposes of the invention.

C. Method for producing a fingerprint containing bands corresponding only to the non-methylated sites.

This method essentially corresponds to the conventional AFLP-technique described in European patent application 0 534 858, and is therefore as such not a separate aspect of the invention. However, the use of this method in the context of the present invention, in particular for generating a reference for comparison to the fingerprints obtained from in the above methods A and/or B, is encompassed by the present application. Method (C) comprises:

1. restricting the starting DNA with a frequent cutter and a methylation sensitive rare cutter;
2. ligating the restriction fragments thus obtained to a fifth adapter for the frequent cutter, as well as a fourth adapter for the methylation sensitive restriction;
3. amplifying the mixture thus obtained, using a primer for the fifth frequent cutter adapter, as well as a primer for the fourth methylation sensitive rare cutter adapter;
4. optionally visualising the amplified fragments thus obtained, preferably by means of a DNA fingerprint.

Method (C) is schematically outlined in FIG. 3, which shows a DNA fragment containing frequent cutter (MseI) sites (again indicated as minor arrows in the sequence), as well as methylated (large arrow with cross) and non-methylated (large arrow) rare cutter (PstI) sites.

The fifth frequent cuter and the fourth rare cutter adapters are again essentially as described in EP-A-0 534 858, or analogous thereto, in that they are suited for use as an adapter in AFLP and that they can be ligated to the cut ends of the restriction fragments (the frequent cutter and rare cutter fragments, respectively).

Again, although these adapters can differ in sequence and/or number of nucleotides from the frequent cutter adapters and rare cutter adapters used in method (A) and (B) above, preferably, for the reasons of convenience discussed above, the fifth adapter for the frequent cutter restriction enzyme is preferably the same as the first or the second—preferably the first—frequency cutter adapter used above, and the fourth rare cutter adapters is the same as the first or second—preferably the second—rare cutter adapter used above. In accordance with this preferred embodiment, the fifth frequent cutter adapter and the fourth rare cutter adapter will be denoted hereinbelow as the "first" MseI adapter and the "second" PstI adapter.

Also, the primers used in conjunction with each of the respective adapters are again preferably essentially the same as the corresponding primers used in the methods (A) and (B) above.

In step 1, the starting DNA is restricted using both the frequent cutter MseI and the rare cutter PstI, in a manner known per se. This restricts both the MseI sites and the non-methylated PstI-sites, but leaves the methylated PstI-sites intact.

Again, the PstI- and MseI-restrictions are preferably carried out simultaneously using a mixture of these enzymes, although it is also possible to use two separate steps.

In step 2, the restricted mixture is ligated to MseI- and PstI-adapters, also in a manner known per se. However, besides the second PstI-adapter, and different from methods A and B above, only one MseI-adapter is used (i.e. either the first or the second), instead of a mixture of two different MseI-adapters.

After ligation of the frequent cutter adapters, a mixture of different restriction fragments is obtained. For the purposes of the invention, these can be distinguished in MseI/MseI-fragments (indicated as VII in FIG. 3), PstI/MseI-fragments (indicated as VIII-A and VIII-A' in FIG. 3), and PstI/PstI-fragments (indicated as IX in FIG. 3). All these fragments may or may not contain the non-restricted methylated PstI-sites (only shown for the MseI/MseI-fragments, as VII-A and VII-A' respectively); as this method is only directed to detecting the non-methylated PstI-sites, these sites are not relevant, nor do they interfere with the resulting fingerprint.

Again, there will be several different fragments of each type present in the mixture obtained after adapter ligation, with differing lengths, depending upon restriction site pattern of the starting DNA. The respective lengths of the fragments VII, VIII and IX will depend on the positions of the MseI-sites and the non-methylated PstI-sites in the starting DNA (but not the methylated PstI-sites). Usually, fragments VII, VIII and IX will differ in length/molecular weight, with the PstI/PstI fragments being appreciably longer than the other fragments due to the relative abundance of the MseI-sites. Because of their differing lengths/molecular weight, these fragments can distinguished using a suitable technique.

To this end, the mixture is amplified in step 3 using suitable primer for the second PstI-adapter, as well a suitable primer for the first MseI-adapters. As mentioned above, these primers are preferably the same as the corresponding primers used in step 6 of method A and/or B above.

The amplification step itself can be carried out in a manner known per se, such as described in EP-A-0 534 858 or in a manner analogous thereto, and is preferably carried out as the two-step amplification of step 6 of method A above, i.e. as a (pre)amplification using a +1-primers for the second PstI-adapter and the first MseI-adapter, followed by selective amplification using +3-primers. In both the pre-amplification and the final amplification, the respective primers can be used in about equal amounts.

Again, the number of selective nucleotides required in a specific primer for a specific application may again be species-dependant. For instance, in maize, +2/+3 amplification and the double +3/+3 selectively for the PstI/MseI primer combination (PC) may be used.

It should be noted that during said amplification, the MseI/MseI-fragments VII-A and VII-A' (i.e. with or without a methylated PstI-site) will not be amplified efficiently due to the formation of loop structures. Also, any PstI/PstI-fragments will generally not be amplified efficiently, as they are to long to be amplified for their full length during the cycle times used.

The resulting amplified fragments are then visualized using a suitable technique, such as the formation of a DNA fingerprint through gel electrophoresis. This fingerprint will show at least bands corresponding to fragments of types VIII-A and and VIII-B, which can be used as a comparison for the fingerprints generated according to method (A) or (B), as discussed below.

D. Determining the methylation pattern of the starting DNA from the fingerprints generated in methods (A), (B) and (C).

The differing fragments, essential for determining the methylation pattern of the starting DNA, that are generated, amplified and detected in each of the methods (A), (B) and (C), are schematically indicated in FIG. 5, which shows a DNA fragment containing frequent cutter (MseI) sites, as well as methylated and non-methylated rare cutter (PstI) sites.

As can be seen from FIG. 5, method A will provide fragments, and bands in the DNA-fingerprint, corresponding to the methylated (I-B and I-C) sites, but not to the non-methylated (III-A and III-A') sites.

Method B will provide fragments, and bands in the DNA-fingerprint, corresponding to the methylated (V-B and V-C) and non-methylated (VI-B and VI-C) sites.

Method C will provide fragments, and bands in the DNA-fingerprint, corresponding to the non-methylated (VIII-B and VIII-C) sites, but not the methylated (VII-A) sites.

Also, as will immediately be clear from FIG. 5, the respective corresponding fragments of interest (i.e. I-B/I-C and V-B/V-C on the one hand, and VI-B/VI-C and VIII-A and VIII-B on the other) will have the same size/molecular weight, and therefore give corresponding bands in the fingerprint, if the respective electrophoreses are run in parallel lanes of the same gel.

Therefore, comparing the fingerprints generated in method (B) to the fingerprint generated in method (A) will provide information on the originally non-methylated sites, which will occur as bands in fingerprint (B) not present in fingerprint (A) (i.e. bands V-A and V-B). Also, these bands will be present in fingerprint (C) (i.e. bands VIII-A and VIII-B).

Information on the originally methylated sites can be derived from comparing either fingerprint (A), fingerprint (B), and preferably both, to fingerprint (C): these will occur as bands present in (A) and (B) (i.e. bands I-B/I-C and VI-B/VI-C), but not in (C).

Also, using well known techniques for analyzing the results from DNA-fingerprints derived from a segregating population, further information can be derived on the position of the methylated and non-methylated sites in the genome, for instance on the relative position of the methylated site to known AFLP-markers or other genetic markers in the starting DNA.

Also, from the restriction site recognised by the methylation sensitive rare cutter used, information can be obtained on the methylated sequence; the use of different methylation sensitive rare cutters providing information on the state of methylation of different sites/sequences in the genome.

The method of the invention can be used as a general tool for detecting DNA-methylation or methylation patterns, both in prokaryotes and eukaryotes, including viruses, yeasts, fungi, bacteria, plants, animals and humans. As such, it can be used to replace known techniques for determining and/or estimating the extend of DNA-methylation, in all applications in which such information is of interest, such as those discussed above.

The method of the invention is particularly suited for applications in which a speedy, qualitative determination of the state of methylation or the methylation pattern, that can be applied to large scale testing, is required. Generally, these will be applications similar to those in which conventional AFLP-techniques are also the technique of choice in determining genetic make-up or RFLP's.

Some non-limiting applications of specific interest are:

distinguishing, identifying or classifying individuals, varieties or species on the basis of their DNA-methylation, by comparing methylation patterns of different individual sources;

fingerprinting of genomes and detecting methylation polymorphisms;

detecting specific methylation patterns corresponding to the presence of specific sequences or genetic traits, as well as inherited DNA-methylation (patterns) and allele-specific methylation (patterns);

estimating the extent of methylation in a DNA or genome;

distinguishing transformed and not-transformed genes or sequences, for instance in the detection of transgenes; and distinguishing replicated and non-replicated DNA in bacteria;

detecting gene silencing or gene activation, and generally investigating the regulation of gene expression, in eukaryotes;

detecting DNA-methylation associated with genetic diseases, genomic imprinting and cancer;

determining the methylation of reporter genes in vivo mutagenicity assays;

detecting methylated DNA-markers;

detecting site-specific methylation (enzymatically or chemically), methylation sensitive sites and/or mutation-associated methylation.

Characterization of heterosis-related DNA methylation changes

Early studies were carried out concerning the quantitative expression of genes in parental inbreds and in hybrids and its possible relation to heterosis and hybrid vigor. Results indicated an increased expression of certain loci in the hybrids. A mechanism involved in regulating the amount of expression output of genes is methylation of cytosine residues in their DNA. Since gene expression is generally negatively correlated with DNA methylation, heterosis (increased expression of certain loci) could be related with a relaxation of methylation at certain crucial CpG- or CpNpG-cytosines.

Data published in the art suggest that inbreeding (selfing) results in increased DNA methylation and, consequently, less gene expression may be expected. The identification of the cytosines (and the genes) which get methylated during the inbreeding process can easily be performed using the methylation AFLP® technique. If the hypothesis "inbreeding depression is the opposite of heterosis" is true, then, simultaneously, we have identified the cytosines (and genes) which get demethylated and come to expression during heterosis.

Cataloging DNA methylation variation

Human DNA sequencing, the flagship endeavor of the Human Genome Project, is entering its decisive phase. Availability of the human genome sequence presents unique scientific opportunities, chief among them the study of natural genetic variation in humans. Genetic or DNA sequence variation is the fundamental raw material for evolution. Importantly, its is also the basis for variations in risk among individuals for numerous medically important, genetically complex human diseases.

Differential DNA methylation, although little studied, may constitute a second important finite source of DNA polymorphism. It is supposed that any two haploid human genomes show multiple sits of methylation polymorphism, although to a less extent than sequence variation. Some of these will have functional implications like conferring susceptibility or resistance, or influencing interaction with environmental factors, whereas many probably not.

The methylation AFLP® technique can be extremely useful in cataloging DNA methylation variation, since it positively displays the unmethylated and the native methylated sites jointly and separately.

Transposons, DNA methylation and gene control

Transposable elements have been used as an effective mutagen and as a tool to clone tagged genes. Insertion of a transposable element into a gene can lead to loss- or gain-of-function, changes in expression pattern, or can have no effect on gene function at all, depending on whether the insertion took place in coding or in non-coding regions of the gene.

In plants, the prevalence of methylated transposons has been known for some time. Methylation of transposase promoters does appear to repress transposon activity. In maize for example, by insertion of Robertson's *Mutator* transposons into promoters, transcription is blocked. However, the resulting method phenotypes can be suppressed by restoration of transcription near the site of insertion. The art suggests that this transcription appears to require transposon methylation. Similarly, insertions of En/Spm transposons into chromosomal gene introns block transcriptional elongation when they are bound to transposase.

When the transposase source is removed (whether by methylation or deletion of the transposase gene), chromosomal gene expression is restored by read-through transcription and splicing. As a result of these mechanisms, strains with multiple suppressible mutations are severly mutant when the transposons are unmethylated, but near normal when they are methylated.

Thus, DNA methylation masks the effects of transposon insertion. Directional 'unmasking' transposon insertions by a till now unknown technique, will reveal interesting mutant phenotypes. The methylation AFLP® technique can play a key role in the identification en localization of the unmasked 'hidden' transposon insertions, and indirectly in the identification and localization of genes.

The invention will now be illustrated by means of the following non-limiting Examples.

EXAMPLES

The Examples below describe the novel PCR-based method of the invention for detecting methylation of restriction sites randomly over the genome. Said method will hereinbelow be referred to as "methylation AFLP™".

The technique is based on (i) the use of a pair of restriction enzymes consisting of a methylation-sensitive rare cutter and a methylation-sensitive frequent cutter, (ii) the comparison of fragments obtained from native and PCR amplified DNA, and (iii) selective amplification of genomic restriction fragments using PCR.

The power of methylation AFLP resides in its positive display of the unmethylated and the native methylated sites jointly and separately, as is obtained after selective amplification of the restriction fragments by PCR. The technique is based on selective amplification of genomic restriction fragments obtained directly from native DNA and also from nonselective amplified DNA by using a methylation-sensitive rare cutter and a methylation-insensitive frequent cutter. Nonselective amplification of restriction fragments is achieved by using only the adapter and restriction site sequence as target sites for primer annealing. Selective amplification is achieved by the use of primers that extend into the restriction fragments, amplifying only those fragments with nucleotides flanking the restriction sites that match the primer extensions.

The advantages of methylation AFLP are manifold: no prior sequence knowledge is needed, a limited set of generic primers is used, a high multiplex ratio (said ratio being a function of the selected specific primer sets) is obtained and a positive display of the unmethylated and native methylated sites is provided. Also, the detection of DNA-methylation is genome-wide. Typically 50–100 restriction fragments are co-amplified and resolved on denaturing polyacrylamide gels. The Examples below will further illustrate how methylation AFLP can be used to estimate the extent of CpG and CpNpG methylation, to detect epialleles and additional sequence polymorphism, and to follow the inheritance of C-methylation.

A variety of techniques to assess the degree of DNA methylation is presently available, which can be divided into sequence-unspecific and sequence-specific methods. The first category can be used to analyse the different types of modified bases and to quantify them, but do not provide any information about the precise location of the modified site within a given nucleic acid sequence. Into this category fall immunological, chromatographic, electrophoretic and spectrophotometric procedures that follow a complete chemical or enzymatic hydrolysis of the target DNA. Another sequence-independent approach involves the use of methylation-sensitive restriction endonucleases where genomic DNA digests obtained with these restriction enzymes are compared using gel electrophoresis (Saluz, H. P. and Jost, J-P. (1993) Jost, P. and Saluz, H. P. (ed.), *DNA Methylation: Molecular Biology and Biological Significance,* Saluz Birkhauser Verlag, Basel, Switzerland). Comparison of fragment lengths and intensities of the resulting digestion patterns on the gel, allows estimation of the proportion of methylated sites.

The second category enables analysis of the precise location of methylated bases within a known DNA sequence. Into this category fall techniques based on the use of pairs of isoschizomeric restriction enzymes that differ in sensitivity to methylation, in combination with Southern-blot analysis (Bird, A. P. and Southern, E. M. (1978), *J. Mol. Biol.* 118, 27–47; Waalwijk, C. and Flavell, R. A. (1978) *Nucl. Acids Res.* 5, 3231–3236) or PCR.

Other PCR-based methods for detecting DNA-methylation have also been reported; one of these PCR-based methods takes advantage of the fact that PCR amplification occurs only if the DNA between the two primer sites remains uncleaved by the methylation-sensitive restriction enzyme HpaII (Singer-Sam, J., LeBon, J. M., Tanguay, R. L. and Riggs A. D. (1990) *Nucl. Acids Res.* 18, 687; Singer-Sam, J., Grant, M., LeBon, J. M., Okuyama, K., Chapman, V., Monk, M. and Riggs, A. D. (1990) *Mol. Cell. Biol.* 10, 4987–4989; Heiskanen M., Syvanen, A. C., Siitari, H., Laine, S. and Palotie, A. (1994) *PCR Methods and Applic.* 4, 26–30). Other PCR-based methods combine PCR with genomic sequencing to identify methylated cytosine residues (Maxam, A. M. and Gilbert, W. (1980) *Methods Enzymol.* 65, 499–560; Pfeiffer, G. P., Steigerwald, S. D., Mueller, P. R., Wold, B. and Riggs A. D. (1989) *Science* 246, 810–813), utilizing the Maxam and Gilbert chemical cleavage reactions carried out on genomic DNA with various additional procedures to enhance the signal from the sequence under investigation.

The bisulfite genomic sequencing technique described by Frommer et al. (Frommer, M., McDonald L. E., Millar, D. S., Collis, C. M., Watt, F., Grigg, G. W., Molloy, P. L. and Paul C. L. (1992) *Proc. Natl. Acad. Sci.* 89, 1827–1831) circumvents the drawbacks of the latter methods by eliminating the chemical cleavage reactions and providing a positive identification of 5-methylcytosine resides. Additional methods have been developed recently which utilize bisulfite treatment of DNA as a starting point for methylation analysis. These include methylation-specific PCR (MSP) (Herman, J. G., Graff, J. R., Myohanen, S., Nelkin, B. D. and Baylin, S. B. (1996) *Proc. Natl. Acad. Sci.,* 93, 9821–9826), restriction enzyme digestion of PCR products amplified from bisulfite-converted DNA (Sadri, R. and Hornsby, P. J. (1996) *Nucleic Acids Res.* 24, 5058–5059; Xiong, Z. and Laird, P. W. (1997) *Nucleic Acids Res.* 25, 2532–2534) and bisulfite treatment of DNA followed by single nucleotide primer extension (Gonzalgo, M. L. and Jones, P. A. (1997) *Nucleic Acids Res.* 25, 2529–2531). With the method of the invention, in contrast with the bisulfite genomic sequencing technique and relatives, the methylation of a virtually unlimited number of loci can be detected.

The principle of the method of the invention is schematically shown in FIG. 6, which gives a schematic representation of the methylation AFLP technique for the enzyme combination (EC) PstI/MseI: 'nonselective amplification' stands for the nonselective MseI/MseI+ amplification; 'selective amplification' stands for the selective PstI/MseI amplification.

The left had column shows the generation of a subset of templates (hereinbelow: "subset A" or "A-templates") in accordance with the general method "A" above, providing restriction fragments with a native methylated PstI site, followed by the selective PstI/MseI amplification procedure.

The middle column shows the generation of a subset of templates (hereinbelow: "subset B" or "B-templates") in accordance with the general method "B" above, providing restriction fragments with a native methylated or unmethylated PstI site, followed by the selective PstI/MseI amplification procedure.

The right hand column shows the generation of a subset of templates (hereinbelow: "subset C" or "C-templates") in accordance with the general method "C" above, representing the restriction fragments with a native unmethylated PstI site, followed by the selective PstI/MseI amplification procedure.

The methylation AFLP technique of the invention is based on the amplification by PCR of three derived subsets (A, B, C) of genomic restriction fragments, differing in (i) digestion of the genomic DNA using two restriction enzymes and (ii) ligated double stranded (ds) adapters.

The general outline of this method is depicted in FIG. 6 for the EC PstI/MseI. Subset A, representing only the restriction fragments with a native methylated PstI cutter site, is obtained in the following way (vide FIG. 6): the genomic DNA is digested to completion with the two restriction enzymes PstI and MseI, and the corresponding ds (AFLP) PstI-adapter* and MseI-adapters$^{(+)}$ are ligated to the unmethylated PstI sites and MseI sites to block the unmethylated PstI ends and to generate template DNA for the nonselective MseI/MseI$^+$ amplification. Two different MseI-adapters are chosen to avoid stem-loop structure forming of the MseI-MseI fragments, which have an inverted repeat at the ends. This is followed by the MseI/MseI$^+$ nonselective amplification of the genomic restriction fragments that may carry an internal methylated PstI site. During this PCR-step, restriction sites lose their methylation imprint. A second digestion of the 'demethylated' PstI sites followed by ligation of the PstI adapter generates templates DNA for further selective PstI/MseI amplification.

The subset B-templates, representing the restriction fragments with native methylated or unmethylated PstI sites, are obtained in a similar way as the subset A-templates, with the exception that the genomic DNA is digested to completion with only MseI, and corresponding ds (AFLP) MseI-adapters$^{(+)}$ are ligated to generate template DNA for the nonselective MseI/MseI$^+$ amplification (see FIG. 6).

The subset C-templates, representing only the restriction fragments with a native unmethylated PstI site are obtained according to the published AFLP procedure (Vos, P., Hogers, R., Bleeker, M., Reijans, M., van de Lee, T., Hornes, M., Frijters, A., Pot, J., Peleman, J., Kuiper, M. and Zabeau, M. (1995) *Nucl. Acids Res.* 23, 4407–4414), in the manner shown in FIG. 6; digestion to completion of the genomic DNA by the EC PstI/MseI, and ligation of the corresponding ds AFLP adapters to the unmethylated PstI sites and MseI sites to generate template DNA for the selective PstI/MseI amplification.

Finally, the A, B and C subsets of templates are simultaneously selectively amplified following the two-step amplification procedure strategy (pre-amplification followed by the AFLP reaction), according to the AFLP fingerprinting method of complex genomes (Vos, P., Hogers, R., Bleeker, M., Reijans, M., van de Lee, T., Hornes, M., Frijters, A., Pot, J., Peleman, J., Kuiper, M. and Zabeua, M. (1995) *Nucl. Acids Res.* 23, 4407–4414.) and then displayed together in adjacent lanes A, B and C of a methylation AFLP fingerprint.

The Examples below are carried out in accordance with the preferred embodiments described above, in that as few different adapters and primers as possible are used. Accordingly, in total only two MseI adapters (i.e. those indicated above as the "first" and "second" MseI adapter), and their two corresponding MseI primers (or primer combinations), and two PstI adapters (i.e. those indicated above as the "first" and "second" PstI adapter) and their two corresponding PstI primers (or primer combinations) are used. In the Examples and Figures, the second MseI adapter is indicated with a (+), and the first PstI adapter is indicated using an (*), i.e. as MseI+ and PstI* respectively. Accordingly, the corresponding second MseI adapter and the corresponding first PstI primer are also indicated with a (+) and a (*), respectively.

Example I

General Description and Protocols Followed

A. Genomic DNAs and enzymes used.

The sources of the genomic DNAs and enzymes used were as follows; Tomato DNA (Near Isogenic Lines (NILs) 83M-S and 83M-R obtained from De Ruiter zonen, The Netherlands; cv. Motelle and Mobox obtained from INRA, Montfavet, France; inbred line RC10 obtained from Enza Zaden, The Netherlands; inbred line 52201 obtained from Rijk Zwaan, The Netherlands), maize DNA (inbred lines B73, Mo17 and A7) was obtained from Dr. M. Motto, Instituto Sperimentale per La Cerealicoltura, Bergamo, Italy; inbred lines D102, DK105, D107, D118, D140, D503, D44, D01, D403, D406, CO125 and W401 were obtained from Dr. W. G. Polmer, University of Hohenheim, Stuttgart, Germany; 88 recombinant inbred lines derived from the cross B73×Mo17 were obtained from Dr. C. W. Stuber, North Carolina State University, Raleigh, N.C., U.S.A.; oilseed rape DNA (12 genotypes obtained from Van der have, The Netherlands) were isolated using a modified CTAB procedure described by Stewart and Via (Sterwart, C. J., Jr and Via L. E. (1993) *Biotechniques* 14, 748–750.) All restriction enzymes were purchased from Pharmacia (Pharmacia LKB Biotechnology AB, Uppsala, Sweden), except for the restriction enzyme MseI, which was purchased from New England Biolabs Inc. (Beverly, Mass., U.S.A.). TaqStart™ Antibody was obtained from Clontech (Clontech Laboratories, Palo Alto, Calif., U.S.A.).

T4 DNA ligase and T4 polynucleotide kinase were also obtained from Pharmacia. All PCR reagents and consumables were obtained from Perkin Elmer Corp. (Norwalk, Conn., U.S.A.). Radioactive reagents were purchased from Amersham (Amersham International plc, Little Chalfont, Buckinghamshire, UK) or Isotopchim (Isotopchim SA, Ganagobie, France).

B. ALFP primers and adapters used.

All oligonucleotides were made on a Biotronic Synostat D DNA-synthesizer (Eppendorf GmbH, Maintal, Germany) or Milligan Expedite 8909 DNA-synthesizer (Millipore Corp. Bedford, Mass., U.S.A.). The quality of the crude oligonucleotides was checked by end-labeling with polynucleotide kinase and [γ-$^{33}$P]ATP and subsequent electrophoresis on 18% denaturing polyacrylamide gels. (Maxam, A. M. and Gilbert, W. (1980) *Methods Enzymol.* 65, 499–540.).

Oligonucleotide adapters and primers for AFLP™ analysis were generally used without further purification when they proved to be >85% full length.

For the rare cutter site two different AFLP adapters were used: 1) the conventional AFLP adapter (called AFLP adapter) as target site for primer annealing and 2) and AFLP adapter servicing as blocking agent (called e.g., PstI-adapter*). Both adapters consist of a core sequence (CORE) and a site-specific sequence (SITE) (Sadri, R. and Hornsby, P. J. (1996) *Nucleic Acids Res.* 24, 5058–5059). The blocking adapters differ from the AFLP adapters only in the core sequence. This is illustrated below for PstI and HpaII-adapters.

|  | CORE | SITE |  |
|---|---|---|---|
| PstI-adapter: | 5'-CTCGTAGACTGCGTACA<br>3'-CATCTGACGCATGT-5' | TGCA-3' | (SEQ ID NO:1)<br>(SEQ ID NO:2) |
| HpaII-adapter: | 5'-CTCGTAGACTGCGTACA-3'<br>3'-CATCTGACGCATGT | GC-5' | (SEQ ID NO:3)<br>(SEQ ID NO:4) |
| PstI-adapter*: | 5'GCATCAGTGCATGCG<br>3'-GTAGTCACGTACGC-5' | TGCA-3' | (SEQ ID NO:5)<br>(SEQ ID NO:6) |
| HpaII-adapter*: | 5'-GCATCAGTGCATGCG-3'<br>3'-GTAGTCACGTACGC | GC-5' | (SEQ ID NO:7)<br>(SEQ ID NO:8) |

The conventional and blocking adapter for MspI and ClaI are identical to those for HpaII.

For the frequent cutter site MseI, also two different AFLP-adapters were used: 1) a MseI-adapter only for non-selective amplification (called MseI-adapter+) and 2) a MseI-adapter (called MseI-adapter) as annealing target site for further nonselective and selective amplification. The MseI-adapters differ only in core sequence. This is illustrated below:

|  | CORE | SITE |  |
|---|---|---|---|
| MseI-adapter: | 5'GACGATGAGTCCTGAG-3'<br>3'-TACTCAGGACTC | AT-5' | (SEQ ID NO: 9)<br>(SEQ ID NO:10) |

-continued

| | CORE | SITE | |
|---|---|---|---|
| MseI-adapter+: | 5'-CTCGTAGACTGCGTACC-3' | (SEQ ID NO:11) | |
| | 3'-CTGACGCATGG | AT-5' | (SEQ ID NO:12) |

AFLP primers consist of three parts, a core sequence, a site-specific sequence (SITE) and a selective extension (EXT) (vide EP-A-0534858). This is illustrated below for PstI- and HpaII-primers with three selective nucleotides (shown as NNN):

| | CORE | SITE | EXT | |
|---|---|---|---|---|
| PstI | 5'-GACTGCGTACA | TGCAG | NNN-3' | (SEQ ID NO:13) |
| HpaII | 5'-GACTGCGTACA | CGG | NNN-3' | (SEQ ID NO:14) |
| ClaI | 5'-GACTGCGTACA | CGAT | NNN-3' | (SEQ ID NO:15) |

ALFLP-primers for MspI and HpaII have a similar architecture. However, it should be noted that the AFLP-primers for PstI, HpaII, MspI and ClaI are desired only for the AFLP adapters.

The two MseI-primers are distinguished in the same way as the two MseI-adapters: the MseI-primer has the MseI-adapter as annealing target site, while MseI-primer+ has the MseI-adapter+ as annealing target site. The difference between the two MseI-primers is shown below:

| | CORE | SITE | EXT | |
|---|---|---|---|---|
| MseI-primer: | 5'-GATGAGTCCTGAG | TAA | NNN-3' | (SEQ ID NO:16) |
| MseI-primer+: | 5'-GTAGACTGCGTACC | TAA-3' | | (SEQ ID NO:17) |

C. Modification of DNA and template preparation.

The protocols A, B and C below describe the generation of A-, B- and C-templates for AFLP reactions using the enzyme combination (EC) PstI/MseI. Protocol C is equivalent to the standard AFLP protocol as described in EP-A-0 534 858 and by Vos et al (Vos, P., Hogers, R., Bleeker, M., Reijans, M., van de Lee, T., Hornes, M., Frijters, A., Pot, J., Peleman, J., Kuiper, M. and Zabeau, M. (1995) *Nucl. Acids Res.* 23, 4407–4414).

Protocol A:

Genomnic DNA (0.5 µg) is incubated for 1 h at 37° C. with 5 U PstI and 5 U MseI in 40 µl 10 mM Tris-HAc pH 7.5, 10 mM MgAc, 50 mM KAc, 5 mM DTT, 50 ng/µl BSA (acetylated). Next, 10 µl of a solution is added, containing 5 pMol PstI-adapter*, 50 pMol MseI-adapter, 50 pMol MseI-adapter+, IU T4 DNA-ligase, 1 mM ATP in 10 mM Tris-HAc pH 7.5, 10 mM MgAc, 50 mM KAc, 5 mM DTT, 50 ng/µl BSA, and the incubation is continued for 3 h at 37° C. Adapters are prepared by adding equimolar amounts of both strands; adapters are not phosphorylated. After ligation, the reaction mixture is diluted to 250 µl with 10 mM Tris-HCl, 0.1 mM EDTA pH 8.0, and used for PCR amplification or stored at −20° C.

Protocol B:

Genomic DNA (0.5 µg) is incubated for 1 h at 37° C. with only 5 U MseI in 40 µl 10 mM Tris-HAc pH 7.5, 10 mM MgAc, 50 mM KAc, 5 mM DTT, 50 ng/µl BSA (acetylated). Next, 10 µl of a solution is added, containing 50 pMol MseI-adapter, 50 pMol MseI-adapter+, 1U T4 DNA-ligase, 1 mM ATP in 1 mM Tris-HAc pH 7.5, 10 mM MgAc, 50 mM KAc, 50 mM DTT, 50 ng/µl BSA, and the incubation is continued for 3 h at 37° C. Adapters are prepared as above (Protocol A). After ligation, the reaction mixture is diluted to 250 µl with 10 mM Tris-HCl, 0.1 mM EDTA pH 8.0, and used for PCR amplification or stored at −20° C.

Protocol C:

Genomic DNA (0.5 µg) is incubated for 1 h at 37° C. with 5 U PstI and 5 U MseI in 40 µl 10 mM Tris-HAc pH 7.5, 10 mM MgAc, 50 mM KAc, 50 mM DTT, 50 ng/µl BSA (acetylated). Next, 10 µl of a solution is added, containing 5 pMol PstI-adapter, 50 pMol MseI-adapter, 1U T4 DNA-ligase, 1 mM ATP in 10 mM Tris-HAc pH 7.5, 10 mM MgAc, 50 mM KAc, 50 mM DTT, 50 ng/µl BSA, and the incubation is continued for 3 h at 37° C. Adapters are prepared as above (Protocol A). After ligation, the reaction mixture is diluted to 500 µl with 10 mM Tris-HCl, 0.1 mM EDTA pH 8.0, and used for PCR amplification or stored at −20° C.

D. Synthesis of unmethylated DNA by nonselective PCR amplification and further modification of DNA and template preparation Synthesis of unmethylated A- and B-templates is performed by nonselective PCR amplification. This nonselective PCR amplification is performed with the following cycle profile for 7 cycles: a 30 s DNA denaturation step at 94° C., a 1 min annealing step at 56° C. and a 2 min extension step at 72° C. Amplifications are performed in 20 µl containing 5 µl-template-DNA, 30 ng MseI-primer, 30 ng MseI-primer+, 0.4 U Taq polymerase, 10 mM Tris-HCl pH 8.3, 1.5 mM MgCl$_2$, 50 mM Kcl and 0.2 mM of all four dNTPs.

After amplification, the reaction mixtures A and B are incubated again for 1 h at 37° C. with 5 U PstI in 40 µl 10 mM Tris-HAc pH 7.5, 10 mM MgAc, 50 mM KAc, 5 mM DTT, 50 ng/µl BSA (acetylated). Next, 10 µl of a solution is added, containing 5 pMol PstI-adapter, 1U T4 DNA-ligase, 1 mM ATP in 10 mM Tris-HAc pH 7.5, 10 mM MgAC, 50 mM KAc, 5 mM DTT, 50 ng/µl BSA (acetylated), and the incubation is continued for 3 h at 37° C.

After ligation, the reaction mixture is diluted to 1000 µl with 10 mM Tris-HCl, 0.1 mM EDTA pH 8.0, and used for PCR amplification or stored at −20° C.

Generation of A- and B-templates for AFLP reactions using methylation-sensitive rare cutters leaving a 5'-extension (e.g. HpaII, MspI, ClaI) involves inactivation of the remaining Taq polymerase after the nonselective amplification, to avoid incorporation of remaining dNTPs after restriction. This is achieved by adding 220 ng TaqStart™ Antibody/U Taq polymerase to the amplification mixture, prior to further restriction and ligation.

E. AFLP Reactions

Amplification reaction conditions are described using DNA templates (A, B and C) for the EC PstI/MseI. With other ECs, the procedure is identical except for the use of appropriate primers.

AFLP fingerprinting of large genomes generally involves an amplification in two steps. The first step of this amplification procedure, named pre-amplification, employs two AFLP primers, one aimed at the PstI-ends and one at the MseI-ends, each having a single selective nucleotide. These primers are not radioactively labelled. Amplifications are performed in 20 $\mu$l containing 5 $\mu$l template-DNA, 30 ng MseI-primer, 30 ng PstI-primer, 0.4 U Taq polymerase, 10 mM Tris-HCl pH 8.3, 1.5 mM $MgCl_2$, 50 mM KCl and 0.2 mM of all four dNTPs.

After pre-amplification, the reaction mixtures are diluted 10-fold with 10 mM Tris-HCl, 0.1 mM EDTA pH=8.0, and used as templates for the second amplification reaction.

The second amplification reaction again employs two oligonucleotide primers, one aimed at the PstI-ends and one at the MseI-ends, each having two or three selective nucleotides. The PstI-primer is radioactively end-labeled using [$\gamma$-$^{33}$P] ATP and T4 polynucleotide kinase. The labelling reactions are performed in 50 $\mu$l 25 mM Tris-HCl pH 7.5, 10 mM $MgCl_2$, 5 mM DTT, 0.5 mM spermidine-3HCl using 500 ng oligonucleotide primer, 100 $\mu$Ci [$\gamma$-$^{33}$P] ATP (1000–3000 Ci/mol) and 10 U T4 polynucleotide kinase. Amplifications are performed in 20 $\mu$l containing 5 $\mu$l template-DNA, 5 ng labeled PstI-primer (0.5 $\mu$l from the labelling reaction mixture), 30 ng MseI-primer, 0.4 U Taq polymerase, 10 mM Tris-HCl pH 8.3, 1.5 mM $MgCl_2$, 50 mM KCl and 0.2 mM of all four dNTPs.

AFLP preamplification reactions are performed for 24 cycles (protocol A and B) and 20 cycles (protocol C) with the following cycle profile: a 30 s DNA denaturation step at 94° C., a 1 min annealing step at 56° C. and a 1 min extension step at 72° C. AFLP reactions with primer having two or three selective nucleotides are performed for 36 cycles with the following cyle profile: a 30 s DNA denaturation step at 94° C., a 30 s annealing step (see below) and a 1 min extension step at 72° C. The annealing temperature in the first cycle is 65° C., and is subsequently reduced each cycle by 0.7° C. for the next 12 cycles, then continued at 56° C. for the remaining 23 cycles. All amplification reactions are performed in a PE-9600 thermocycler (Perkin Elmer Corp. Norwalk, Conn. U.S.A.).

F. Gel Analysis

Following amplification, reaction products are mixed with an equal volume (20 $\mu$l) of formamide dye (98% formamide, 10 mM EDTA pH 8.0, and bromophenol blue and xylene cyanol as tracking dyes). The resulting mixture is heated for 3 min at 90° C., then quickly cooled on ice. Each sample (2 $\mu$l) was loaded on a 5% denaturing (sequencing) polyacrylamide gel (Maxam, A. M. and Gilbert, W. (1980) *Methods Enzymol.* 65, 499–560). The gel matrix is prepared using 5% acrylamide, 0.25% methylene bisacryl, 7.5 M urea in 50 mM Tris/50 mM Boric acid/1 mM EDTA (pH 8.3). To 100 ml of gel solution 500 $\mu$l of 10% APS and 100 $\mu$l TEMED is added and gels are cast using a SequiGen 38×50 cm gel apparatus (Biorad Laboratories Inc., Hercules, Calif., U.S.A.). 100 mM Tris/100 mM Boric acid/2 ml EDTA was used as running buffer. Electrophoresis is performed at constant power, 110 W, for about 2 hours. After electrophoresis, gels are fixed for 30 min in 10% acetic acid, rinsed with water for 10 min, dried on the glass plates and exposed to Fujix phosphorimage screens for 16 h. Fingerprint patterns are visualized using a Fujix BAS-2000 phosphorimage analysis system (Fuji Photo Film Company Ltd., Japan).

Example II

Methylation AFLP Fingerprinting of Large Genomes

Initial experiments with methylation AFLP fingerprinting of plant genomic DNAs indicated that the complexity of the template libraries is of the same order as in the standard AFLP protocol. For maize, however, the number of the fragments detected in the B reaction (corresponding to the fragments of the A and C reaction jointly) by PstI+2/MseI+3 primer combinations (PCs) is substantially elevated, so 'tuning' to a slightly higher selectivity of the PCs is desirable and results in combined PstI PCs, e.g. PstI+AGW or PstI+AGS), where W stands for A and T jointly, and where S stands for C and G jointly.

FIGS. 7A and 7B show methylation AFLP fingerprints of genomic DNAs from the three maize inbred lines A7, B73 and Mo17. The two panels show PstI/MseI fingerprints, corresponding with the following PCs (from left to right): I. PstI+AGW/MseI+CTT, and II. PstI+AGS/MseI+CTT. Lane A, B and C represent the corresponding A, B and C restriction fragments, referring to the native methylated state of the rare cutter sites. The molecular weight size range of the fingerprints is 200–500 nucleotides.

Theoretically, every band present in lane A or lane C should also be present in lane B, because lane B represents both the native methylated and unmethylated rare cutter sites jointly. As seen in FIG. 2, for PCs I, this is true for more than 90% of the fragments in lane A and C. In some cases (e.g. PC II), however, the percentage of fragments in lane A and C present in lane B can be low. An explanation for this is the following: short MseI-MseI restriction fragments have a competitive advantage over the longer MseI-MseI restriction fragments in the nonselective amplification. Consequently, rare cutter restriction sites (methylated or not), on average residing more on long MseI-MseI restriction fragments, will have a selective disadvantage. Subsequent restriction and ligation of the underrepresented fragments will generate a reduced amount of templates.

Although, as suggested by the fingerprints, large plant genomes consist predominantly of unique AFLP fragments, the presence of repetitive DNA is reflected by fragments of moderate (arrow 1) or high (arrow 2) band intensities in FIGS. 7A and 7B, in the good accordance with the correlation that exists between the AFLP band intensity and the original number of restriction fragments (Vos, P., Hogers, R., Bleeker, M., Reijans, M., van de Lee, T., Hornes, M., Frijters, A., Pot, J., Peleman, J., Kuiper, M. and Zabeau, M. (1995) *Nucl. Acids Res.* 23, 4407–4414). Since these multicopy restriction fragments are more abundantly present in lane A than in lane C, it can be concluded that moderate and highly repetitive sequences are strongly methylated. It should also be noted that the excessive use of primers by these multicopy PstI-MseI restriction fragments also leads to an underrepresentation of fragments in lane B.

Example III

Estimating the Extent of $^{5m}$CpNpG as Presented in PstI-sites of Some Large Plant Genomes In plants the modified C at position 5 ($^{m5}$C) is not only confined to CpG dinucleotides as is in animals, but also occurs at a variety of other cytosine containing dinucleotides, all of which are part of the basic trinucleotide CpNpG where N can be any nucleotide (Gruenbaum, Y., Naveh-Maney, T., Cedar, H. and Razin, A., 1981, *Nature* 292, 860–862) The restriction enzyme PstI, having 5'-CTGCAG-3' as recognition site, containing two CpNpG trinucleotides, is sensitive to methylation at the 5'-C and the 3'-C (McClelland, M., Nelson, M. and Raschke, E. (1994) *Nucl. Acids Res.* 22, 3640–3659). Whether simultaneous methylation of both C's of the PstI recognition site is possible, is not clear. A mean percentage±standard error of methylated PstI-sites in the nuclear DNA of tomato, maize and oilseed rape, are given in Table 1.

Table 1. Mean percentages±standard error of methylated PstI-sites and $^{5m}$CpNpG as presented in PstI-sites in the nuclear DNA of tomato, maize and oilseed rape, and published mean percentages $^{5m}$C residues (expressed as % $^{5m}$C/$^{5m}$C+C) in the nuclear DNA of tomato and maize, N=number of genotypes assayed. n=total number of PstI/MseI restriction fragments counted.

| Species | N | % PstI-sites methylated | % CpNpG-sites methylated | n | %$^{5m}$C/$^{5m}$C + C |
|---|---|---|---|---|---|
| tomato | 6 | 39.75 ± 1.00 | 19.88 ± 0.50 | 219–248 | 22.8 (19) |
| maize | 12 | 50.78 ± 1.33 | 25.39 ± 0.67 | 753–820 | 28.9 (20) |
| oilseed rape | 6 | 33.19 ± 0.62 | 16.60 ± 0.31 | 548–609 | |

It is clear from Table 1 that variation in the percentage of methylated PstI-sites is very low within a species. Using the percentage of $^{5m}$CpNpG-sites as presented in PstI-sites, calculated as half the number of methylated PstI-sites, as estimation of the percentage of $^{5m}$C residues in the nuclear DNA (expressed as $^{5m}$C/$^{5m}$C+C), results in percentages $^{5m}$C residues very similar to published percentages, based on HPLC analysis (Messuguer, R., Ganal, M. W., Steffens, J. C., and Tanksley, S. D., 1991, *Plant Mol. Biol.* 16, 753–770 and Montero, L. M. et al., 1992, *Nucl. Acids Res.* 20, 3207–3210), for tomato and maize (see Table 1). Therefore, methylation of only one C residue in the PstI recognition site is highly probable.

Example IV

Estimating the Extent of $^{5m}$CpG as Presented in HpaII-, MspI- and ClaI-sites in Some Large Plant Genomes MspI and HpaII (methylation isoschizomers) have the same recognition site 5'-CCGG-3', containing one CpG dinucleotide. However, MspI is sensitive to 5'-$^{5m}$C, whereas HpaII is sensitive to methylation at position 5 of either C (McClelland, M., Nelson, M. and Raschke, E. (1994) *Nucl. Acids Res.* 22, 3640–3659). Therefore, MspI and HpaII are appropriate for estimating the extent of $^{5m}$CpG. The extent of $^{5m}$CpG methylation by using HpaII and MspI as methylation-sensitive rare cutters is measured as the difference in the number of bands counted in a MspI and a HpaII fingerprint in lane C; the difference in the number of bands counted in a MspI and a HpaII fingerprint in lane A must give the same result. The percentages of $^{5m}$CpG sites in the nuclear DNA of tomato and maize, as presented in HpaII- and MspI-sites, are measured only for one genotype/species, and are given in Table 2.

Another methylation-sensitive restriction enzyme ClaI, having the CpG-dinucleotide containing recognition site 5'-ATCGAT-3', and affected by $^{5m}$CpG (McClelland, M., Nelson, M. and Raschke, E. and (1994) *Nucl. Acids Res.* 22, 3640–3659) was also found to be suitable as rare cutter in the detection of $^{5m}$CpG. The percentages of $^{5m}$CpG as presented in HpaII-, MspII- and ClaI-sites in the nuclear DNA of tomato, maize and oilseed rape, are measured for only one genotype/species, and are given in Table 2.

Table 2. Percentages of $^{5m}$CpG in the nuclear DNA of tomato, maize and oilseed rape, as presented in HpaII-, MspI- and ClaI-sites. n=total number of restriction fragments counted.

| Species | $^{5m}$CpG as presented in ClaI-sites | n | $^{5m}$CpG as presented in HpaII/MspI-sites | n |
|---|---|---|---|---|
| tomato (cv.52201) | 57.9 | 2833 | 57.6 | 2169 |
| maize (B73) | 53.9 | 2694 | 39.6 | 1791 |
| oilseed rape (T528) | 48.4 | 2973 | | |

In tomato, a similar percentage of $^{5m}$CpG as presented in ClaI-sites is obtained as presented in either HpaII- or MspI-sites, in contrast with maize. Estimations of the percentage of $^{5m}$C residues as presented in ClaI-sites in the nuclear DNA of tomato, mais and oilseed rape is significantly higher than the the corresponding percentages $^{5m}$C residues as presented in PstI-sites. This can suggest that the majority of $^{5m}$C residues in the tomato, maize and oilseed rape genome exist at CpG sites.

Example V $^{5m}$C Polymorphism and Its Inheritance

AFLP primarily detects variation of the primary DNA sequence, either base substitutions or DNA rearrangements. Nucleotides modified by methylation are not considered to be a part of the primary nucleotide sequence of an individual. This nucleotide modification, resulting from a post-replicative event at defined but not all target sequences (i.e. CpG and CpNpG), represents two additional forms of DNA polymorphism: (i) polymorphism reflecting the variation in the primary nucleotide sequence of the methylated restriction site and/or variation in the restriction size ($^m$AFLP method), and (ii) allele-specific methylation ($^{asm}$AFLP markers). Since DNA-methylation is also the only source of allelic difference between epialleles, $^{asm}$AFLP markers are epiallelic markers. Since methylation AFLP provides a positive display of the native methylated sites, it allows exploitation of this additional sources of DNA polymorphism.

For methylation polymorphism to be useful in e.g. AFLP mapping studies, it must be stably inherited. FIG. 8A shows the segregation of a number of $^m$AFLP markers in a Recombinant Inbred (RI) population derived from the cross B73× Mo17. The band intensities segregate into two distinct classes, homozygous absent and homozygous present, approximating the Mendelian 1:1 segregation. To identify possible $^{asm}$AFLP marker pairs, the following criteria are applied: (i) an AFLP band and a $^m$AFLP band might be epialleles when derived from different parents, with the same PC; (ii) the AFLP and $^m$AFLP marker map to the same locus (complementary segregation). FIGS. 8A and 8B show the segregation of a pair of $^{asm}$AFLP markers in the RI population. The band intensities segregate into two distinct classes, homozygous absent and homozygous present. Of a total of 673 mapped AFLP+$^m$AFLP markers, generated by a set of 14 PstI/MseI PCs, $^m$AFLP markers account for 44.6%, which is in good accordance with the 50.78% methylated PstI-sites in the maize genome (Table 1), while hardly 1% of the marker alleles behave like epialleles.

As can be seen from the above description and Examples, the method of invention can be considered a DNA fingerprinting technique that detects genomic restriction fragments and resembles in that respect the AFLP technique, with the major difference that methylation AFLP displays native methylated sites too, but in general only if they are located in the recognition site of the obligate methylation-sensitive rare cutter. As for AFLP, the multiplex ratio is high (50–100 restriction fragments) and is a function of (i) the cleavage frequency of the methylation-sensitive rare cutter enzyme and (ii) the number and nature of the selective bases of the specific primer set.

Also, as demonstrated in the Examples, the method of the invention can be used for estimating the extent of $^{5m}$CpNpG, resp. $^{5m}$CpG, as presented in PstI-, resp. ClaI-, HpaI- and MspI-sites in the genome of few crops. Although generalization of these estimates to percentages $^{5m}$CpNpG and $^{5m}$CpG in the genome, irrespective the recognition site, may in some cases not be fully representative as methylation of C can be biased by the nature of its flanking nucleotides (recognition site), or by the percentage G+C of the genomic region it resides (CG-islands), the method of the invention will still provide valuable information to the artisan.

Although hereinabove the invention was particularly described with respect to the use of methylation AFLP to estimate the extent of $^{5m}$CpG and $^{5m}$CpNpG as presented in some recognition sites in the genome, the invention and its possible uses are not only limited to that. Modification of C at other positions than 5 (e.g. $^{m4}$C), or modified nucleotides other than C (e.g. $^{m6}$A), whether present in a symmetrical or a non-symmetrical dinucleotide (e.g. $^{5m}$CpC), are reported ((Gruenbaum, Y., Naveh-Maney, T., Cedar, H. and Razin, A., 1981, *Nature* 292, 860–862); Selker, E. U., Fritz, D. Y. and Singer, M. J., 1993, *Science* 262, 1724–1728; and Meyer, P., Niedenhof, I., ten Lohuis, M., 1994, *The EMBO Journal* 13, 2084–2088).

Methylation AFLP can also be used with advantage to estimate the low prevalence of these minor nucleotide modifications presented by recognition sites of methylation-sensitive rare cutters, and to shed a light on their distributions over the genome.

Methylation AFLP allows the exploitation of two additional forms of DNA polymorphism: (i) polymorphism reflecting variation in the primary nucleotide sequence of the methylated restriction site and/or variation in the restriction fragment size, and (ii) allele-specific methylation. Hardly 1% of the marker alleles behave like epialleles.

By monitoring the segregation of $^m$AFLP and $^{asm}$AFLP markers in a RI population, it was shown that (i) C-methylation segregates in perfect accordance with the primary target sequence, while (ii) the few epialleles observed in the parents inherit in a Mendelian fashion to the offspring.

Like AFLP markers, most $^m$AFLP markers correspond to unique positions in the genome, and, hence, can be exploited as landmarks in and as bridging tools between genetic and physical maps (Vos, P., Hogers, R., Bleeker, M., Reijans, M., van de Lee, T., Hornes, M., Frijters, A., Pot, J., Peleman, J., Kuiper, M. and Zabeau, M. (1995) *Nucl. Acids Res.* 23, 4407–4414). Therefore, methylation AFLP may be useful in genomic research. Native methylated sites are present on cloned DNA segments, e.g., yeast artificial chromosomes (YACs) as unmethylated sites. Hence, native methylated sites can not be distinguished from native unmethylated sites on a physical map. However, ligning up the physical map with a genetic map containing $^m$AFLP markers, helps to identify native methylated sites on the physical map.

More than in plant genetics, in human genetics the epigenetic effects of DNA methylation at CpG-island containing promoters is well documented. Due to its sensitive, reliable and quantitative nature, methylation AFLP is an attractive technique to determine the DNA methylation levels at specific gene loci like tumor-suppressor genes and to trace imprinted genes.

Note: AFLP™ is a trademark of Keygene N.V.

What is claimed is:

1. A method for determining the methylation pattern or for distinguishing between methylated and non-methylated restriction enzyme cleavage sites in a starting DNA which contains or is suspected of containing methylated cleavage sites, comprising:

comparing at least two DNA fingerprints so as to determine the methylation pattern or to distinguish between methylated and non-methylated restriction enzyme cleavage sites, wherein said DNA fingerprints are generated using at least two different DNA fingerprinting procedures selected from the group consisting of:

(A) DNA fingerprinting procedure (A), containing fragments visualized as bands, where one end of the fragments is a restriction enzyme cleavage site that is methylated in the starting DNA;

(B) DNA fingerprinting procedure (B), containing fragments visualized as bands, where one end of the fragments is a restriction enzyme cleavage site that is either methylated or non-methylated in the starting DNA; and (C) DNA fingerprinting procedure (C), containing fragments visualized as bands, where both ends of the fragments are non-methylated in the starting DNA, wherein:

DNA fingerprinting procedure (A) comprises:

(1) digesting the starting DNA with a frequent cutter restriction enzyme and a methylation-sensitive rare cutter restriction enzyme at their cleavage sites to generate first restriction fragments;

(2) ligating the first restrictions fragments to first and second adapters for the cleavage site of the frequent cutter restriction enzyme and to a first adapter for the cleavage site of the methylation-sensitive rare cutter restriction enzyme to form a first set of adapter-ligated restriction fragments;

(3) amplifying the adapter-ligated restriction fragments by using primers complementary to the first and second adapters for the cleavage site of the frequent cutter restriction enzyme to thereby remove methylation imprint from methylated sites;

(4) digesting the amplified adapter-ligated restriction fragments with a methylation-sensitive rare cutter restriction enzyme to generate second restriction fragments;

(5) ligating the second restriction fragments to a second adapter for the cleavage site of the methylation-sensitive rare cutter restriction enzyme to form a second set of adapter-ligated restriction fragments;

(6) amplifying the second set of adapter-ligated restriction fragments by using a primer complementary to the first or second adapter for the cleavage site of the frequent cutter restriction enzyme and a primer complementary to the second adapter for the cleavage site of the methylation-sensitive rare cutter restriction enzyme to thereby obtain a DNA fingerprint, DNA fingerprinting procedure (B) comprises:

(1) digesting the starting DNA with only a frequent cutter restriction enzyme at its cleavage site to generate first restriction fragments;

(2) ligating the first restriction fragments to third and fourth adapters for the cleavage site of the frequent cutter restriction enzyme to form a first set of adapter-ligated restriction fragments;

(3) amplifying the first set of adapter-ligated restriction fragments by using primers complementary to the third and fourth adapters to thereby remove methylation imprint from methylated cleavage sites;

(4) digesting the amplified adapter-ligated restriction fragments with a methylation-sensitive rare cutter restriction enzyme to generate second restriction fragments;

(5) ligating the second restriction fragments to a third adapter for the cleavage site of the methylation-sensitive rare cutter restriction enzyme to form a second set of adapter-ligated restriction fragments;

(6) amplifying the second set of adapter-ligated restriction fragments by using a primer complementary to the third adapter for the cleavage site of the methylation-sensitive rare cutter restriction enzyme and a primer complementary to the third or fourth adapter for the cleavage site of the frequent cutter restriction enzyme to thereby obtain a DNA fingerprint, and DNA fingerprinting procedure (C) comprises:

(1) digesting the starting DNA with a frequent cutter restriction enzyme and a methylation-sensitive rare cutter restriction enzyme at their cleavage sites to generate restriction fragments;

(2) ligating the restriction fragments to an adapter for the cleavage site of the frequent cutter restriction enzyme and to an adapter for the cleavage site of the methylation-sensitive rare cutter restriction enzyme to form adapter-ligated restriction fragments;

(3) amplifying the adapter-ligated restriction fragments by using a primer complementary to the adapter for the cleavage site of the frequent cutter restriction enzyme and a primer complementary to the adapter for the cleavage site of the methylation-sensitive rare cutter restriction enzyme to thereby obtain a DNA fingerprint.

2. The method of claim 1, wherein at least two of the DNA fingerprints generated are run in separate lanes of an electrophoresis gel.

3. The method of claim 1, wherein the first and second adapters for the cleavage site at the frequent cutter restriction enzyme in DNA fingerprinting procedure (A) are the same as the third and fourth adapters for the cleavage site of the frequent cutter restriction enzyme in DNA fingerprinting procedure (B).

4. The method of claim 1, wherein the second and third adapters for the cleavage site of the methylation-sensitive rare cutter restriction enzyme are the same.

5. The method of claim 1, wherein the frequent cutter restriction enzyme is selected from the group consisting of MseI and TaqI and the methylation-sensitive rare cutter restriction enzyme is selected from the group consisting of PstI, HpaII, MspI, ClaI, HhaI, EcoRII, BbvI, PvuII, XmaI, SmaI, NciI, AvaI, HaeII, SalI, and XhoI.

6. A method for distinguishing, identifying or classifying individuals, varieties or species on the basis of their DNA methylation, for fingerprinting genomes and detecting methylation polymorphism, or for detecting specific methylation patterns indicative of the presence of specific sequences or genetic traits, inherited DNA-methylation, or allele-specific methylation, comprising comparing the methylation patterns of DNA from different individual sources obtained using the method of claim 1.

7. A method for distinguishing transformed and non-transformed genes or sequences or for distinguishing replicated and non-replicated DNA in bacteria, comprising comparing the methylation pattern of DNA from a sample source against the methylation pattern of DNA from a non-transformed or non-replicated source, wherein the methylation patterns are obtained using the method of claim 1.

8. A method for investigating or determining the regulation of gene expression in eukaryotes, comprising comparing the methylation pattern of DNA from a sample source against the methylation pattern of DNA from a source with gene silencing or gene activation, wherein the methylation patterns are obtained using the method of claim 1.

9. A method for detecting genetic disorders, comprising comparing the methylation pattern of DNA from an individual with the methylation pattern of DNA known to be associated with genetic diseases and increased susceptibility to mutagenesis and cancer, wherein the methylation pattern of DNA from the individual is obtained using the method of claim 1.

10. A method for detecting a gene for estimating the extent of methylation in a DNA or genome or for detecting methylated DNA markers, comprising comparing the methylation pattern of DNA from an individual source with the methylation pattern of a gene or methylated DNA markers, wherein the methylation patterns are obtained using the method of claim 1.

11. A method for obtaining a DNA fingerprint, containing fragments visualized as bands, where one end of the fragments is a restriction enzyme cleavage site that is methylated in a starting DNA, comprising:

(1) digesting the starting DNA with a frequent cutter restriction enzyme and a methylation-sensitive rare cutter restriction enzyme at their cleavage sites to generate first restriction fragments;

(2) ligating the first restriction fragments to first and second adapters for the cleavage site of the frequent cutter restriction enzyme and to a first adapter for the cleavage site of the methylation-sensitive rare cutter restriction enzyme to form a first set of adapter-ligated restriction fragments;

(3) amplifying the first set of adapter-ligated restriction fragments by using primers complementary to the first and second adapters for the cleavage site of the frequent cutter restriction enzyme to thereby remove methylation imprint from methylated sites;

(4) digesting the amplified adapter-ligated restriction fragments with a methylation-sensitive rare cutter restriction enzyme to generate second restriction fragments;

(5) ligating the second restriction fragments to a second adapter for the cleavage site of the methylation-sensitive rare cutter restriction enzyme to form a second set of adapter-ligated restriction fragments;

(6) amplifying the second set of adapter-ligated restriction fragments by using a primer complementary to the first or second adapter for the cleavage site of the frequent cutter restriction enzyme and a primer complementary to the second adapter for the cleavage site of the methylation-sensitive rare cutter restriction enzyme to thereby obtain a DNA fingerprint.

12. The method of claim 11, wherein the frequent cutter restriction enzyme is selected from the group consisting of MseI and TaqI and the methylation-sensitive rare cutter restriction enzyme is selected from the group consisting of PstI, HpaII, MspI, ClaI, HhaI, EcoRII, BbvI, PvuII, XmaI, SmaI, NciI, AvaI, HaeII, SalI, and XhoI.

13. A method for distinguishing, identifying or classifying individuals, varieties or species on the basis of their DNA methylation, for fingerprinting genomes and detecting methylation polymorphism, or for detecting specific methylation patterns indicative of the presence of specific sequences or genetic traits, inherited DNA-methylation, or allele-specific methylation, comprising comparing the methylation patterns of DNA from different individual sources obtained using the method of claim 11.

14. A method for distinguishing transformed and non-transformed genes or sequences or for distinguishing replicated and non-replicated DNA in bacteria, comprising comparing the methylation pattern of DNA from a sample source against the methylation pattern of DNA from a non-transformed or non-replicated source, wherein the methylation patterns are obtained using the method of claim 11.

15. A method for investigating or determining the regulation of gene expression in eukaryotes, comprising comparing the methylation pattern of DNA from a sample source against the methylation pattern of DNA from a source with gene silencing or gene activation, wherein the methylation patterns are obtained using the method of claim 11.

16. A method for detecting genetic disorders, comprising comparing the methylation pattern of DNA from an individual with the methylation pattern of DNA known to be associated with genetic diseases and increased susceptibility to mutagenesis and cancer, wherein the methylation pattern of DNA from the individual is obtained using the method of claim 11.

17. A method for detecting a gene for estimating the extent of methylation in a DNA or genome or for detecting methylated DNA markers, comprising comparing the methylation pattern of DNA from an individual source with the methylation pattern of a gene or methylated DNA markers, wherein the methylation patterns are obtained using the method of claim 11.

18. A method for obtaining a DNA fingerprint, containing fragments visualized as bands, where one end of the fragments is a restriction enzyme cleavage site that is either methylated or non-methylated, comprising:

(1) digesting the starting DNA with only a frequent cutter restriction enzyme at its cleavage site to generate first restriction fragments;

(2) ligating the first restriction fragments to first and second adapters for the cleavage site of the frequent cutter restriction enzyme to form a first set of adapter-ligated restriction fragments;

(3) amplifying the adapter-ligated restriction fragments by using primers complementary to the first and second adapters to thereby remove methylation imprint from methylated cleavage sites;

(4) digesting the amplified adapter-ligated restriction fragments with a methylation-sensitive rare cutter restriction enzyme to generate second restriction fragments;

(5) ligating the second restriction fragments to an adapter for the cleavage site of the methylation-sensitive rare cutter restriction enzyme to form a second set of adapter-ligated restriction fragments;

(6) amplifying the second set of adapter-ligated restriction fragments by using a primer complementary to the adapter for the cleavage site of the methylation-sensitive rare cutter restriction enzyme and a primer complementary to the first or second adapters for the cleavage site of the frequent cutter restriction enzyme to thereby obtain a DNA fingerprint.

19. The method of claim 18, wherein the frequent cutter restriction enzyme is selected from the group consisting of MseI and TaqI and the methylation-sensitive rare cutter restriction enzyme is selected from the group consisting of PstI, HpaII, MspI, ClaI, HhaI, EcoRII, BbvI, PvuII, XmaI, SmaI, NciI, AvaI, HaeII, SalI, and XhoI.

20. A method for distinguishing, identifying or classifying individuals, varieties or species on the basis of their DNA methylation, for fingerprinting genomes and detecting methylation polymorphism, or for detecting specific methylation patterns indicative of the presence of specific sequences or genetic traits, inherited DNA-methylation, or allele-specific methylation, comprising comparing the methylation patterns of DNA from different individual sources obtained using the method of claim 18.

21. A method for distinguishing transformed and non-transformed genes or sequences or for distinguishing replicated and non-replicated DNA in bacteria, comprising comparing the methylation pattern of DNA from a sample source against the methylation pattern of DNA from a non-transformed or non-replicated source, wherein the methylation patterns are obtained using the method of claim 18.

22. A method for investigating or determining the regulation of gene expression in eukaryotes, comprising comparing the methylation pattern of DNA from a sample source against the methylation pattern of DNA from a source with gene silencing or gene activation, wherein the methylation patterns are obtained using the method of claim 18.

23. A method for detecting genetic disorders, comprising comparing the methylation pattern of DNA from an individual with the methylation pattern of DNA known to be associated with genetic diseases and increased susceptibility to mutagenesis and cancer, wherein the methylation patterns of DNA from the individual is obtained using the method of claim 18.

24. A method for detecting a gene for estimating the extent of methylation in a DNA or genome or for detecting methylated DNA markers, comprising comparing the methylation pattern of DNA from an individual source with the methylation pattern of a gene or methylated DNA markers, wherein the methylation patterns are obtained using the method of claim 18.

* * * * *

SEQUENCE LISTING

<160> NUMBER OF SEQ ID NOS:   17

<210> SEQ ID NO 1
<211> LENGTH: 21
<212> TYPE: DNA
<213> ORGANISM: Unknown
<220> FEATURE:
<223> OTHER INFORMATION: synthetic
<221> NAME/KEY: misc_feature
<223> OTHER INFORMATION: PstI-adapter
<221> NAME/KEY: misc_feature
<222> LOCATION: (4)..(17)
<223> OTHER INFORMATION: complementary to SEQ ID NO:2

<400> SEQUENCE: 1
ctcgtagact gcgtacatgc a                                              21

<210> SEQ ID NO 2
<211> LENGTH: 14
<212> TYPE: DNA
<213> ORGANISM: Unknown
<220> FEATURE:
<223> OTHER INFORMATION: synthetic

```
<221> NAME/KEY: misc_feature
<223> OTHER INFORMATION: PstI-adapter
<221> NAME/KEY: misc_feature
<222> LOCATION: (1)..(14)
<223> OTHER INFORMATION: complementary to SEQ ID NO:1

<400> SEQUENCE: 2
tgtacgcagt ctac                                                    14

<210> SEQ ID NO 3
<211> LENGTH: 17
<212> TYPE: DNA
<213> ORGANISM: Unknown
<220> FEATURE:
<223> OTHER INFORMATION: synthetic
<221> NAME/KEY: misc_feature
<223> OTHER INFORMATION: HpaII-adapter
<221> NAME/KEY: misc_feature
<222> LOCATION: (4)..(17)
<223> OTHER INFORMATION: complementary to SEQ ID NO:4

<400> SEQUENCE: 3
ctcgtagact gcgtaca                                                 17

<210> SEQ ID NO 4
<211> LENGTH: 16
<212> TYPE: DNA
<213> ORGANISM: Unknown
<220> FEATURE:
<223> OTHER INFORMATION: synthetic; HpaII-adapter
<221> NAME/KEY: misc_feature
<223> OTHER INFORMATION: HapaII-adapter
<221> NAME/KEY: misc_feature
<222> LOCATION: (2)..(16)
<223> OTHER INFORMATION: complementary to SEQ ID NO:3

<400> SEQUENCE: 4
cgtgtacgca gtctac                                                  16

<210> SEQ ID NO 5
<211> LENGTH: 19
<212> TYPE: DNA
<213> ORGANISM: Unknown
<220> FEATURE:
<223> OTHER INFORMATION: synthetic
<221> NAME/KEY: misc_feature
<223> OTHER INFORMATION: PstI-adapter
<221> NAME/KEY: misc_feature
<222> LOCATION: (2)..(15)
<223> OTHER INFORMATION: complementary to SEQ ID NO:6

<400> SEQUENCE: 5
gcatcagtgc atgcgtgca                                               19

<210> SEQ ID NO 6
<211> LENGTH: 14
<212> TYPE: DNA
<213> ORGANISM: Unknown
<220> FEATURE:
<223> OTHER INFORMATION: synthetic
<221> NAME/KEY: misc_feature
<223> OTHER INFORMATION: PstI-adapter
<221> NAME/KEY: misc_feature
<222> LOCATION: (1)..(14)
<223> OTHER INFORMATION: complementary to SEQ ID NO:5

<400> SEQUENCE: 6
cgcatgcact gatg                                                    14
```

```
<210> SEQ ID NO 7
<211> LENGTH: 15
<212> TYPE: DNA
<213> ORGANISM: Unknown
<220> FEATURE:
<223> OTHER INFORMATION: synthetic
<221> NAME/KEY: misc_feature
<223> OTHER INFORMATION: HapII-adapter
<221> NAME/KEY: misc_feature
<222> LOCATION: (2)..(15)
<223> OTHER INFORMATION: complementary to SEQ ID NO:8

<400> SEQUENCE: 7
gcatcagtgc atgcg                                                    15

<210> SEQ ID NO 8
<211> LENGTH: 16
<212> TYPE: DNA
<213> ORGANISM: Unknown
<220> FEATURE:
<223> OTHER INFORMATION: synthetic
<221> NAME/KEY: misc_feature
<223> OTHER INFORMATION: HpaII-adapter
<221> NAME/KEY: misc_feature
<222> LOCATION: (2)..(16)
<223> OTHER INFORMATION: complementary to SEQ ID NO:7

<400> SEQUENCE: 8
cgcgcatgca ctgatg                                                   16

<210> SEQ ID NO 9
<211> LENGTH: 16
<212> TYPE: DNA
<213> ORGANISM: Unknown
<220> FEATURE:
<223> OTHER INFORMATION: synthetic
<221> NAME/KEY: misc_feature
<223> OTHER INFORMATION: MseI-adapter
<221> NAME/KEY: misc_feature
<222> LOCATION: (5)..(16)
<223> OTHER INFORMATION: complementary to SEQ ID NO:10

<400> SEQUENCE: 9
gacgatgagt cctgag                                                   16

<210> SEQ ID NO 10
<211> LENGTH: 14
<212> TYPE: DNA
<213> ORGANISM: Unknown
<220> FEATURE:
<223> OTHER INFORMATION: synthetic
<221> NAME/KEY: misc_feature
<223> OTHER INFORMATION: MseI-adapter
<221> NAME/KEY: misc_feature
<222> LOCATION: (2)..(16)
<223> OTHER INFORMATION: complementary to SEQ ID NO:9

<400> SEQUENCE: 10
tactcaggac tcat                                                     14

<210> SEQ ID NO 11
<211> LENGTH: 17
<212> TYPE: DNA
<213> ORGANISM: Unknown
<220> FEATURE:
<223> OTHER INFORMATION: synthetic
<221> NAME/KEY: misc_feature
<223> OTHER INFORMATION: MseI-adapter
<221> NAME/KEY: misc_feature
<222> LOCATION: (6)..(17)
<223> OTHER INFORMATION: complementary to SEQ ID NO:12
```

```
<400> SEQUENCE: 11
ctcgtagact gcgtacc                                              17

<210> SEQ ID NO 12
<211> LENGTH: 13
<212> TYPE: DNA
<213> ORGANISM: Unknown
<220> FEATURE:
<223> OTHER INFORMATION: synthetic
<221> NAME/KEY: misc_feature
<223> OTHER INFORMATION: MseI-adapter
<221> NAME/KEY: misc_feature
<222> LOCATION: (3)..(13)
<223> OTHER INFORMATION: complementary to SEQ ID NO:11

<400> SEQUENCE: 12
taggtacgca gtc                                                  13

<210> SEQ ID NO 13
<211> LENGTH: 19
<212> TYPE: DNA
<213> ORGANISM: Unknown
<220> FEATURE:
<223> OTHER INFORMATION: synthetic
<221> NAME/KEY: misc_feature
<223> OTHER INFORMATION: PstI-primer
<221> NAME/KEY: misc_feature
<223> OTHER INFORMATION: N is unknown

<400> SEQUENCE: 13
gactgcgtac atgcagnnn                                            19

<210> SEQ ID NO 14
<211> LENGTH: 17
<212> TYPE: DNA
<213> ORGANISM: Unknown
<220> FEATURE:
<223> OTHER INFORMATION: synthetic
<221> NAME/KEY: misc_feature
<223> OTHER INFORMATION: HpaII-primer
<221> NAME/KEY: misc_feature
<223> OTHER INFORMATION: N is unknown

<400> SEQUENCE: 14
gactgcgtac acggnnn                                              17

<210> SEQ ID NO 15
<211> LENGTH: 18
<212> TYPE: DNA
<213> ORGANISM: Unknown
<220> FEATURE:
<223> OTHER INFORMATION: synthetic
<221> NAME/KEY: misc_feature
<223> OTHER INFORMATION: ClaI-primer
<221> NAME/KEY: misc_feature
<223> OTHER INFORMATION: N is unknown

<400> SEQUENCE: 15
gactgcgtac acgatnnn                                             18

<210> SEQ ID NO 16
<211> LENGTH: 19
<212> TYPE: DNA
<213> ORGANISM: Unknown
<220> FEATURE:
<223> OTHER INFORMATION: synthetic
<221> NAME/KEY: misc_feature
<223> OTHER INFORMATION: MseI-primer
```

```
<221> NAME/KEY: misc_feature
<223> OTHER INFORMATION: N is unknown

<400> SEQUENCE: 16
gatgagtcct gagtaannn                                              19

<210> SEQ ID NO 17
<211> LENGTH: 17
<212> TYPE: DNA
<213> ORGANISM: Unknown
<220> FEATURE:
<223> OTHER INFORMATION: synthetic
<221> NAME/KEY: misc_feature
<223> OTHER INFORMATION: MseI-primer

<400> SEQUENCE: 17
gtagactgcg tacctaa                                                17
```